(12) United States Patent
Xiao

(10) Patent No.: US 7,049,420 B2
(45) Date of Patent: May 23, 2006

(54) REGULATION OF HUMAN PROSTASIN-LIKE SERINE PROTEASE

(75) Inventor: Yonghong Xiao, Cambridge, MA (US)

(73) Assignee: Bayer HealthCare AG, Leverkusen (DE)

( * ) Notice: Subject to any disclaimer, the term of this patent is extended or adjusted under 35 U.S.C. 154(b) by 313 days.

(21) Appl. No.: 10/311,591

(22) PCT Filed: Jun. 22, 2001

(86) PCT No.: PCT/EP01/07116

§ 371 (c)(1),
(2), (4) Date: Dec. 18, 2002

(87) PCT Pub. No.: WO01/98466

PCT Pub. Date: Dec. 27, 2001

(65) Prior Publication Data

US 2004/0141962 A1    Jul. 22, 2004

Related U.S. Application Data

(60) Provisional application No. 60/277,612, filed on Mar. 22, 2001, provisional application No. 60/213,474, filed on Jun. 23, 2000.

(51) Int. Cl.
*C07H 21/04* (2006.01)
(52) U.S. Cl. .................... 536/23.2; 536/23.1
(58) Field of Classification Search ............... 536/23.1, 536/23.2
See application file for complete search history.

(56) References Cited

FOREIGN PATENT DOCUMENTS

| WO | WO 01/16290 | 3/2001 |
|---|---|---|
| WO | WO 01/24815 | 4/2001 |
| WO | WO 01/75067 | 10/2001 |
| WO | WO 01/98467 | 12/2001 |
| WO | WO 01/98468 | 12/2001 |

OTHER PUBLICATIONS

Verma et al. (Nature 1997; 389: 239-242).*
Marshal (Science 1995; 269 (5227): 1050-1055).*
Eck et al. (Goodman & Gilman's The Pharmacological Basis of Therapeutics (1996), 9th Edition, Chapter 5, McGraw-Hill, NY).*
Juengst (British Medical Journal 2003; 326: 1410-1411.*
Rubanyi (Mol. Aspects Med. 2001; 22: 113-142.*
Database JBC Online "Online!" htpp://www.jbc.org. (XP002935257) cited in Yu J X et al Molecular Cloning, Tissue-Specific Expression, and Cellular Localization of Human Prostasin MRNA, Journal of Biological Chemistry, vol. 270 (22), 1995, 13483-13489.

* cited by examiner

*Primary Examiner*—Jeffrey Siew
*Assistant Examiner*—Brandon Fetterolf
(74) *Attorney, Agent, or Firm*—Banner & Witcoff, Ltd.

(57) ABSTRACT

Reagents which regulate human prostasin-like enzyme activity and reagents which bind to human prostasin-like enzyme gene products can be used to regulate human prostasin-like enzyme activity. Such regulation is particularly useful for treating metastasis of malignant cells, tumor angiogenesis, inflammation, atherosclerosis, neurodegenerative diseases, and pathogenic infections.

9 Claims, 12 Drawing Sheets

Fig. 1

```
        atgagagggg tttcctgtct ccaggtcctg ctccttctgg tgctggcctg
cgggcagccc cgcatgtcca gtcggatcgt tgggggccgg gatggccggg acggagagtg
gccgtggcag gcgagcatcc agcatcgtgg ggcacacgtg tgcggggggt cgctcatcgc
cccccagtgg gtgctgacag cggcgcactg cttccccagg agggcactgc cagctgagta
ccgcgtgcgc ctgggggcgc tgcgtctggg ctccacctcg ccccgcacgc tctcggtgcc
cgtgcgacgg gtgctgctgc ccccggacta ctccgaggac ggggcccgcg gcgacctggc
actgctgcag ctgcgtcgcc cggtgcccct gagcgctcgc gtccaacccg tctgcctgcc
cgtgcccggc gcccgcccgc cgcccggcac accatgccgg gtcaccggct ggggcagcct
ccgcccagga gagtggcgac cgctacaagg agtaagggtg ccgctgctgg actcgcgcac
ctgcgacggc ctctaccacg tgggcgcgga cgtgccccag gctgagcgca ttgtgctgcc
tgggagtctg tgtgccggct accccagggg ccacaaggac gcctgccagg gtgattctgg
gggacctctg acctgcctgc agtctgggag ctgggtcctg gtgggcgtgg tgagctgggg
caagggttgt gccctgccca accgtccagg ggtctacacc agtgtggcca catatagccc
ctggattcag gctcgc
```

Fig. 2

MRGVSCLQVL LLLVLACGQP RMSSRIVGGR DGRDGEWPWQ ASIQHRGAHV CGGSLIAPQW

VLTAAHCFPR RALPAEYRVR LGALRLGSTS PRTLSVPVRR VLLPPDYSED GARGDLALLQ

LRRPVPLSAR VQPVCLPVPG ARPPPGTPCR VTGWGSLRPG EWRPLQGVRV PLLDSRTCDG

LYHVGADVPQ AERIVLPGSL CAGYPQGHKD ACQGDSGGPL TCLQSGSWVL VGVVSWGKGC

ALPNRPGVYT SVATYSPWIQ AR

Fig. 3

| MAQKGVLGPG AVAGQWPWQV | QLGAVAILLY | LGLLRSGTGA | EGAEAPCGVA | PQARITGGSS |
| --- | --- | --- | --- | --- |
| SITYEGVHVC DAKVSTLKDI | GGSLVSEQWV | LSAAHCFPSE | HHKEAYEVKL | GAHQLDSYSE |
| IPHPSYLQEG TGWGHVAPSV | SQGDIALLQL | SRPITFSRYI | RPICLPAANA | SFPNGLHCTV |
| SLLTPKPLQQ KDACQGDSGG | LEVPLISRET | CNCLYNIDAK | PEEPHFVQED | MVCAGYVEGG |
| PLSCPVEGLW RVVPQTQESQ | YLTGIVSWGD | ACGARNRPGV | YTLASSYASW | IQSKVTELQP |

PDSNLCGSHL AFSSAPAQGL LRPILFLPLG LALGLLSPWL SEH

Fig. 4

```
ccaggctgag    cgcattgtgc    tgcctgggag    tctgtgtgcc    ggctacccc
agggccacaa
ggacgcctgc    caggtgtgca    cccagcctnc    ccagcctccg    gagtccctc
cctgtgccca
gcaccctccc    tccctgaact    ccaggaccca    ggacatcca     actnaggctc
aggatcctgg
cctccaacct    agaggcacca    cgncaggggt    ctggaaccct    gagaactgaa
gtcctgggag
ggctgggacc    taggctcctc    tttct
```

Fig.5 atgagagggg tttcctgtct ccaggtcctg ctccttctgg tgctggcctg cgggcagccc
cgcatgtcca gtcggatcgt tggggggccgg gatggccggg acggagagtg gccgtggcag
gcgagcatcc agcatcgtgg ggcacacgtg tgcggggggt cgctcatcgc ccccagtgg
gtgctgacag cggcgcactg cttccccagg agggcactgc cagctgagta ccgcgtgcgc
ctgggggcgc tgcgtctggg ctccacctcg ccccgcacgc tctcggtgcc cgtgcgacgg
gtgctgctgc ccccggacta ctccgaggac gggggcccgcg gcgacctggc actgctgcag
ctgcgtcgcc cggtgcccct gagcgctcgc gtccaacccg tctgcctgcc cgtgcccggc
gcccgcccgc cgcccggcac accatgccgg gtcaccggct ggggcagcct ccgcccagga
gtgccccctcc cagagtggcg accgctacaa ggagtaaggg tgccgctgct ggactcgcgc
acctgcgacg gcctctacca cgtgggcgcg gacgtgcccc aggctgagcg cattgtgctg
cctgggagtc tgtgtgccgg ctacccccag ggccacaagg acgcctgcca gggtgattct
gggggacctc tgacctgcct gcagtctggg agctgggtcc tggtgggcgt ggtgagctgg
ggcaagggtt gtgccctgcc caaccgtcca ggggtctaca ccagtgtggc cacatatagc
ccctggattc aggctcgcgt caagattact aaatactaac cgggtgaagg agaacctgaa
gcaagtggtg ggggtcctca aaccacctgg ttcatacaag gacctgccta taaccaaaaa
ccttctgctt caagcaaaag ccaaaaagct aaggcaaccc aaca

Fig.6

MRGVSCLQVL   LLLVLACGQP   RMSSRIVGGR   DGRDGEWPWQ
ASIQHRGAHV CGGSLIAPQW
VLTAAHCFPR   RALPAEYRVR   LGALRLGSTS   PRTLSVPVRR
VLLPDYSED GARGDLALLQ
LRRPVPLSAR   VQPVCLPVPG   ARPPPGTPCR   VTGWGSLRPG
VPLPEWRPLQ GVRVPLLDSR
TCDGLYHVGA   DVPQAERIVL   PGSLCAGYPQ   GHKDACQGDS
GGPLTCLQSG SWVLVGVVSW

GKGCALPNRP GVYTSVATYS PWIQARVKIT KY

FIG. 7

BLASTP - Query = 140_TR1; Hit = swiss|Q16651|PSS8_HUMAN

This hit is scoring at : 2e-64 (expectation value)
      Alignment length (overlap) : 243
      Identities : 47 %
      Scoring matrix : BLOSUM62 (used to infer consensus pattern)
      Database searched : nrdb

```
Q:                                                                    24
SRIVGGRDGRDGEWPWQASIQHRGAHVCGGSLIAPQWVLTAAHCFPRRALPAEYRVRLGA
            :RI.GG...       G:WPWQ.SI.:..G.HVCGGSL::..QWVL:AAHCFP..
...Y.V:LGA
H:                                                                    43
ARITGGSSAVAGQWPWQVSITYEGVHVCGGSLVSEQWVLSAAHCFPSEHHKEAYEVKLGA
                                        TRYPSIN_HIS

LRLGSTSPRTLSVPVRRVLLPPDYSEDGARGDLALLQLRRPVPLSARVQPVCLPVPGARP
            :L.S S. .      .::  ::     P.Y  ::G::GD:ALLQL.RP:..S.
::P:CLP...A.

HQLDSYSEDAKVSTLKDIIPHPSYLQEGSQGDIALLQLSRPITFSRYIRPICLPAANASF

PPGTPCRVTGWGSLRPG----
EWRPLQGVRVPLLDSRTCDGLYHVGADVPQAERIVLPGS
            P G. C.VTGWG.:.P.      . :PLQ :.VPL:...TC: LY::.A.
P:....V ...
               PNGLHCTVTGWGHVAPSVSLLTPKPLQQLEVPLISRETCNCLYNIDAK-
PEEPHFVQEDM

LCAGYPQGHKDACQGDSGGPLTCLQSGSWVLVGVVSWGKGCALPNRPGVYTSVATYSPWI
            :CAGY :G KDACQGDSGGPL:C  .G W.L.G:VSWG..C.. NRPGVYT
.::Y:.WI

VCAGYVEGGKDACQGDSGGPLSCPVEGLWYLTGIVSWGDACGARNRPGVYTLASSYASWI
                                        TRYPSIN_SER

QAR        262
               Q::
               QSK        284
```

BLOCKS
FIG. 8

Prosite search results:

| Access# | From->To | Name | Doc# |
|---|---|---|---|
| PS00134 | 62->68 | TRYPSIN_HIS | PDOC00124 |
| PS00135 | 210->222 | TRYPSIN_SER | PDOC00124 |

FIG. 9

```
         BLOCKS search result

AC#              Description                    Strength  Score
BL00495N         Apple domain proteins.           1945     1599

AA#  201 AGYpqGhKDACqGDSGGPLtClqSGsWvLVGvvSW

BL00021B         Kringle domain proteins.         1547     1567

AA#      50 CGGSLIAPQWVLTAAHCF

BL01253G         Type I fibronectin domain proteins  1641  1553

AA#      208 kDACQGDSGGPLtC

BL00134A         Serine proteases, trypsin family,
                            histidine p          1500     1549

AA#      50 CGGSLIAPQWVLTAAHC

BL00021D         Kringle domain proteins.         1556     1444

AA#         217  GPLtCLQsGsWVLVGVVSWGkGCALPNRPGVYTsVAtYsPWI
(SEQ ID NO:9)

BL01253H         Type I fibronectin domain proteins.  1765  1414

AA#         227 wvLVGvvSWGkGCalpNrPGVYTsVAtYspWIQaR  (SEQ  ID
NO:10)

BL00495K        Apple domain proteins.           1821     1353

AA#          52 GSLIapQWVLTAAHCFprraLPaeyRVrlGaLr  (SEQ   ID
NO:11)

BL01253E        Type I fibronectin domain proteins.  1661  1329

AA#         122 RpvpLSArVQPVCLPvPGARPPpGTpCrVtGWGsLrp (SEQ ID
NO:12)

BL01253D        Type I fibronectin domain proteins.  1398  1293

AA#      50 CGGSLIAPqWVLTA

BL00134B        Serine proteases, trypsin family,
                            histidine p          1289     1257

AA#      209 DACQGDSGGPLTCLqSGSWVLVGV

BL00134C        Serine proteases, trypsin family,
                            histidine p          1245     1250
```

|        |     |                         |      |      |
|--------|-----|-------------------------|------|------|
| AA#    | 245 | PGVYTSVATYSPWI          |      |      |
| BL00021C |   | Kringle domain proteins. | 1309 | 1231 |
| AA#    | 133 | VCLPvPGARPPPGTpCrVTGWG  |      |      |
| BL004950 |   | Apple domain proteins.  | 1756 | 1229 |
| AA#    | 236 | GkGCAlpnRPGVYTsVAtYspWIqar |   |      |

Fig. 10

BLASTP - alignment of 140_v2_TR1 against swiss|Q16651|PSS8_HUMAN
   This hit is scoring at : 4e-67 (expectation value)
   Alignment length (overlap) : 244
   Identities : 48 %
   Scoring matrix : BLOSUM62 (used to infer consensus pattern)
   Database searched : nrdb_1_;

Q:                                                                            24
SRIVGGRDGRDGEWPWQASIQHRGAHVCGGSLIAPQWVLTAAHCFPRRALPAEYRVRLGA
       :RI.GG... G:WPWQ.SI.:.G.HVCGGSL.::.QWVL:AAHCFP.. ...Y.V:LGA
H:                                                                           43
ARITGGSSAVAGQWPWQVSITYEGVHVCGGSLVSEQWVLSAAHCFPSEHHKEAYEVKLGA

LRLGSTSPRTLSVPVRRVLLPPDYSEDGARGDLALLQLRRPVPLSARVQPVCLPVPGARP
       :L.S S. . .:: :: P.Y ::G::GD:ALLQL.RP:..S. ::P:CLP....A.

HQLDSYSEDAKVSTLKDIIPHPSYLQEGSQGDIALLQLSRPITFSRYIRPICLPAANASF

PPGTPCRVTGWGSLRPGVPLPEWRPLQGVRVPLLDSRTCDGLYHVGADVPQAERIVLPGS
       P G. C.VTGWG.:.P.V.L . :PLQ :.VPL:...TC: LY::.A. P:....V ...
       PNGLHCTVTGWGHVAPSVSLLTPKPLQQLEVPLISRETCNCLYNIDAK-PEEPHFVQEDM

LCAGYPQGHKDACQGDSGGPLTCLQSGSWVLVGVVSWGKGCALPNRPGVYTSVATYSPWI
       :CAGY :G KDACQGDSGGPL:C .G W.L.G:VSWG..C.. NRPGVYT .::Y:.WI

VCAGYVEGGKDACQGDSGGPLSCPVEGLWYLTGIVSWGDACGARNRPGVYTLASSYASWI

QARV    267
       Q::V
       QSKV    285

Fig. 11

Gene Prediction:

The target 140 is constructed mainly from Genscan output on genomic clone AC005570.1 (chromosome 16). 3' end (from bp799 to the end) was based on EST BF689477, part of which does not align to any genomic sequence currently available. That's why from bp802 on the target 140 does not align to any available genomic sequence.

Exon/intron structure (Q=140_v2; H=AC005570.1)

Exon 1
Q:     1 atgagagggggtttcctgtctccaggtcctgctccttctggtgctgg     46
H: 25745 atgagagggggtttcctgtctccaggtcctgctccttctggtgctgg  25790

Exon 2
Q:    47 cctgcgggcagccccgcatgtccagtcggatcgttgggggccgggatggccgggacgga
H: 26331 g)cctgcgggcagccccgcatgtccagtcggatcgttgggggccgggatggccgggacgga gagtggccgtggcaggcgagcatccagcatcgtggggcacacgtgtgcggggggtcgctc
         gagtggccgtggcaggcgagcatccagcatcgtggggcacacgtgtgcggggggtcgctc
                           *BF689477 starts atcgcccccagtgggtgctgacagcggcgcactgcttccccag     209
         atcgcccccagtgggtgctgacagcggcgcactgcttccccag(g  26493

Exon 3
Q:   210    gagggcactgccagctgagtaccgcgtgcgcctgggggcgctgcgtctgggctccac
H: 26646 cag)gagggcactgccagctgagtaccgcgtgcgcctgggggcgctgcgtctgggctccac

...

ccgggtcaccggctggggcagcctccgcccaggag    481
         ccgggtcaccggctggggcagcctccgcccaggag  26917

Exon 4
Q:   482    tgcccctcccagagtggcgaccgctacaaggagtaagggtgccgctgctggactcgcg
H: 27121 ag)tgcccctcccagagtggcgaccgctacaaggagtaagggtgccgctgctggactcgcg
             inserted based on BF689477)

...

gcctgggagtctgtgtgccggctaccccagggccacaaggacgcctgccag    651
         gcctgggagtctgtgtgccggctaccccagggccacaaggacgcctgccag(g  27290

Exon 5
Q: 652    ggtgattctgggggacctctgacctgcctgcagtctgggagctgggtcctggtgggc
H: 27490 cag)ggtgattctgggggacctctgacctgcctgcagtctgggagctgggtcctggtgggc

...

gccacatatagcccctggattcaggctcgc    798
     gccacatatagcccctggattcaggctcgc(gtca 27636

The rest is from BF689477:
140_v2:   795 ...tcgcgtcaagattactaaatactaa... 819 (cds ends, 3'utr starts)
BF689477: 646 ...tcgcgtcaagattactaaatactaa... 670

...

agctaaggcaacccaaca   944
     agctaaggcaacccaaca   795

GENSCAN output (on AC005570.1):
Gn.Ex Type S .Begin ...End .Len Fr Ph I/Ac Do/T CodRg P.... Tscr..
----- ---- - ------ ------ ---- -- -- ---- ---- ----- ----- ------
 2.00 Prom + 18802 18841  40                        -0.71
 2.01 Init + 25745 25790  46  1  1  53  92   91 0.718   4.80
 2.02 Intr + 26331 26493 163  1  1 103  76  152 0.918  15.05
 2.03 Intr + 26646 26917 272  0  2  76  94  340 0.999  31.12
(bp481, BF689477 seems to have a few extra bases here)
 2.04 Intr + 27133 27290 158  2  2  64  69  222 0.653  18.14
(bp639)
 2.05 Intr + 27490 27636 147  0  0 103  -4  100 0.699   3.24
(bp786)

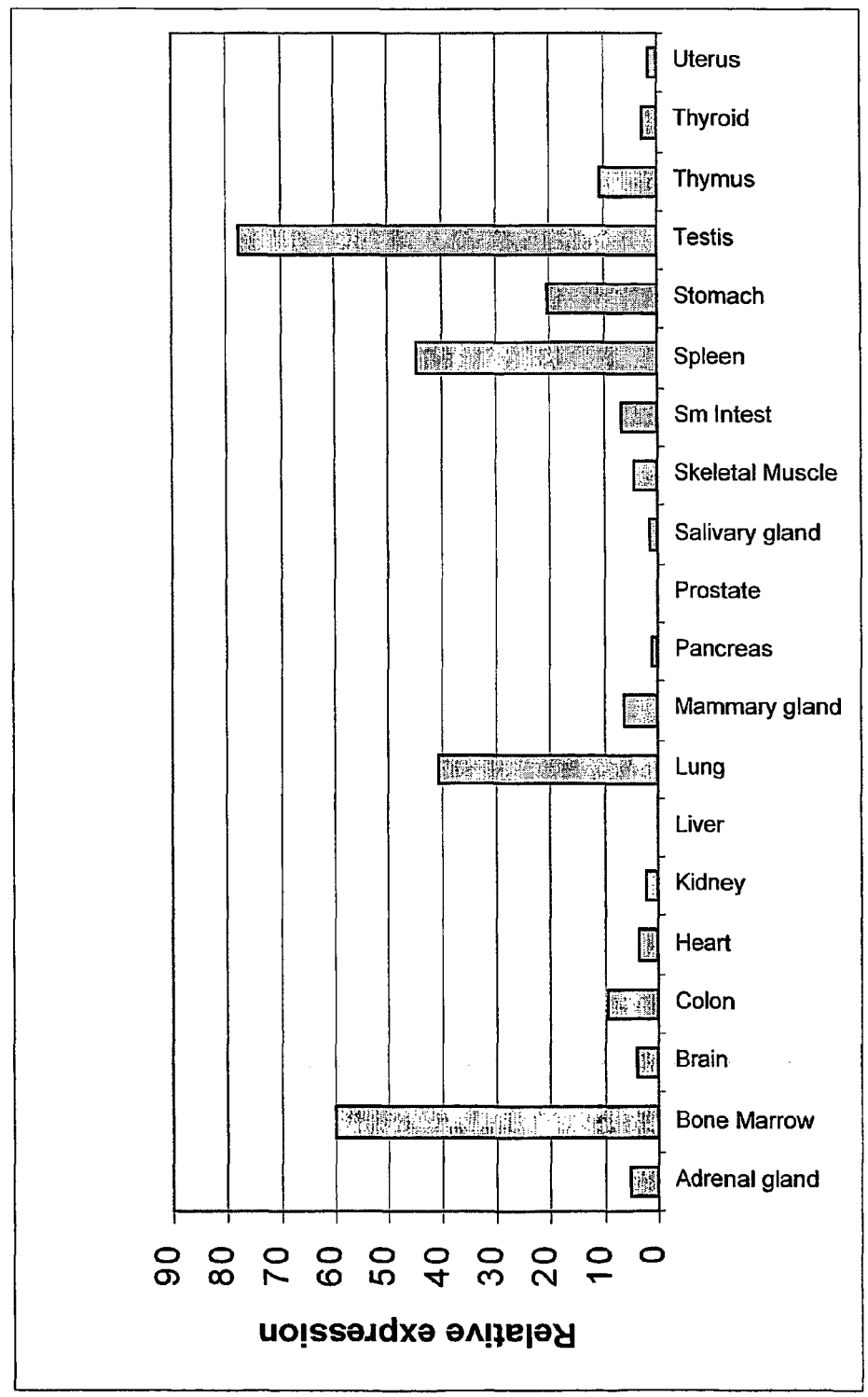
Fig. 12 Relative expression of prostasin-like enzyme in various human tissues.

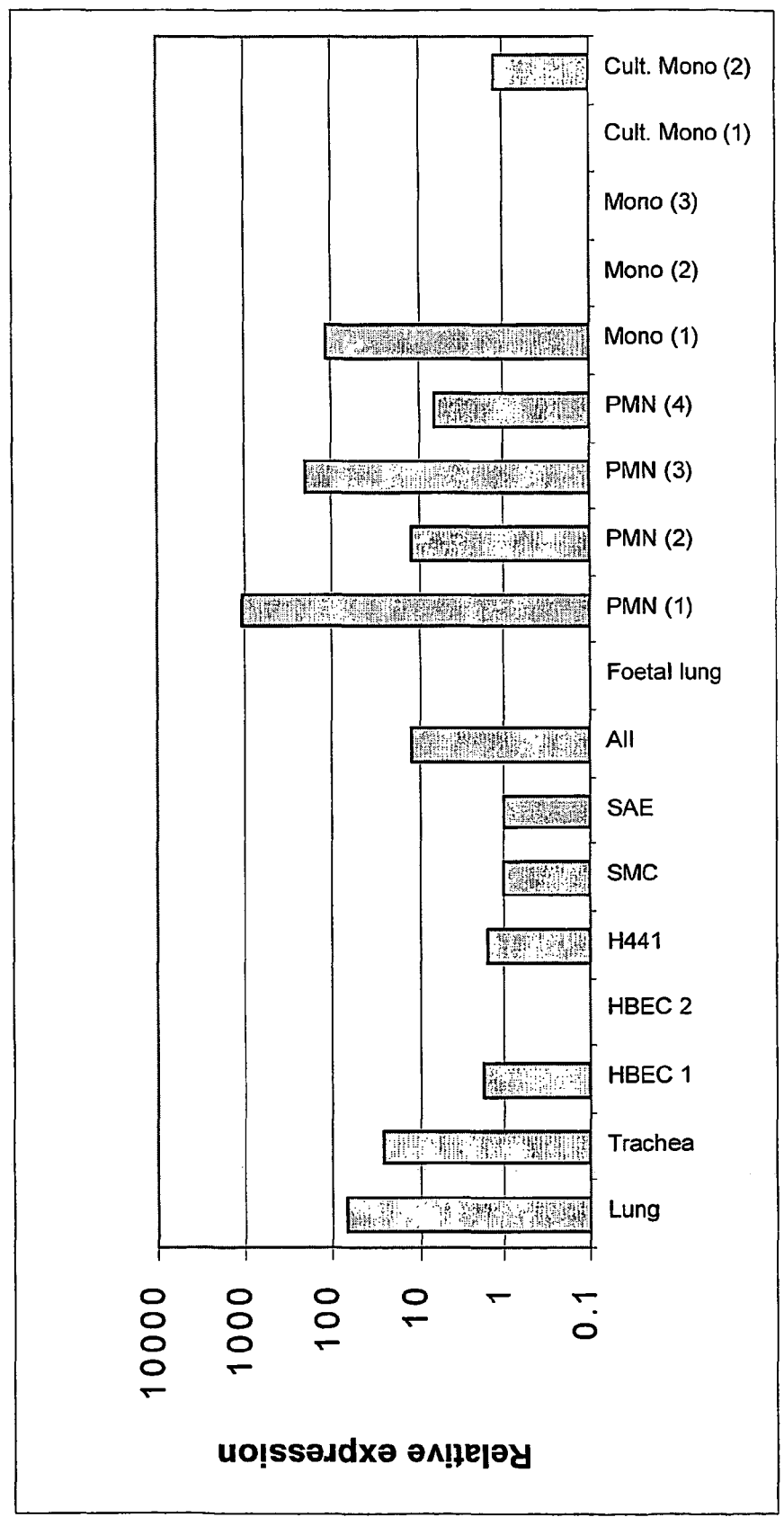
FIG. 13 Relative expression of prostasin-like enzyme in various human respiratory tissues and cells.

REGULATION OF HUMAN PROSTASIN-LIKE SERINE PROTEASE

This application is a National Stage application of co-pending PCT application PCT/EP01/07116 filed Jun. 22, 2001, which was published in English under PCT Article 21(2) on Dec. 27, 2001, which claims the benefit of U.S. provisional application Ser. No. 60/213,474 filed Jun. 23, 2000 and Ser. No. 60/277,612 filed Mar. 22, 2001.

TECHNICAL FIELD OF THE INVENTION

The invention relates to the area of enzyme regulation. More particularly, the invention relates to the regulation of human prostasin-like enzyme activity.

BACKGROUND OF THE INVENTION

Serine proteases are involved in a variety of biological functions, including cell-cell communication, cell migration, and tissue remodeling. Thus, there is a need in the art to identify additional human serine proteases which can be regulated to provide therapeutic effects.

SUMMARY OF THE INVENTION

It is an object of the invention to provide reagents and methods of regulating human prostasin-like enzyme activity. These and other objects of the invention are provided by one or more of the embodiments described below.

One embodiment of the invention is a prostasin-like enzyme polypeptide comprising an amino acid sequence selected from the group consisting of:
amino acid sequences which are at least about 50% identical to the amino acid sequence shown in SEQ D NO: 2 or SEQ ID NO: 6; and
the amino acid sequence shown in SEQ ID NO: 2 or SEQ ID NO: 6.

Yet another embodiment of the invention is a method of screening for agents which decrease extracellular matrix degradation. A test compound is contacted with a prostasin-like enzyme polypeptide comprising an amino acid sequence selected from the group consisting of:
amino acid sequences which are at least about 50% identical to the amino acid sequence shown in SEQ ID NO: 2 or SEQ ID NO: 6; and
the amino acid sequence shown in SEQ ID NO: 2 or SEQ ID NO: 6.

Binding between the test compound and the prostasin-like enzyme polypeptide is detected. A test compound which binds to the prostasin-like enzyme polypeptide is thereby identified as a potential agent for decreasing extracellular matrix degradation. The agent can work by decreasing the activity of the prostasin-like enzyme.

Another embodiment of the invention is a method of screening for agents which decrease extracellular matrix degradation. A test compound is contacted with a polynucleotide encoding a prostasin-like enzyme polypeptide, wherein the polynucleotide comprises a nucleotide sequence selected from the group consisting of:
nucleotide sequences which are at least about 50% identical to the nucleotide sequence shown in SEQ ID NO: 1 or SEQ ID NO: 5; and
the nucleotide sequence shown in SEQ ID NO: 1 or SEQ ID NO: 5.

Binding of the test compound to the polynucleotide is detected. A test compound which binds to the polynucleotide is identified as a potential agent for decreasing extracellular matrix degradation. The agent can work by decreasing the amount of the prostasin-like enzyme through interacting with the prostasin-like enzyme mRNA.

Another embodiment of the invention is a method of screening for agents which regulate extracellular matrix degradation. A test compound is contacted with a prostasin-like enzyme polypeptide comprising an amino acid sequence selected from the group consisting of:
amino acid sequences which are at least about 50% identical to the amino acid sequence shown in SEQ ID NO: 2 or SEQ ID NO: 6; and
the amino acid sequence shown in SEQ ID NO: 2 or SEQ ID NO: 6.

A prostasin-like enzyme activity of the polypeptide is detected. A test compound which increases prostasin-like enzyme activity of the polypeptide relative to prostasin-like enzyme activity in the absence of the test compound is thereby identified as a potential agent for increasing extracellular matrix degradation. A test compound which decreases prostasin-like enzyme activity of the polypeptide relative to prostasin-like enzyme activity in the absence of the test compound is thereby identified as a potential agent for decreasing extracellular matrix degradation.

Even another embodiment of the invention is a method of screening for agents which decrease extracellular matrix degradation. A test compound is contacted with a prostasin-like enzyme product of a polynucleotide which comprises a nucleotide sequence selected from the group consisting of:
nucleotide sequences which are at least about 50% identical to the nucleotide sequence shown in SEQ ID NO: 1 or SEQ ID NO: 5; and
the nucleotide sequence shown in SEQ ID NO: 1 or SEQ ID NO: 5.

Binding of the test compound to the prostasin-like enzyme product is detected. A test compound which binds to the prostasin-like enzyme product is thereby identified as a potential agent for decreasing extracellular matrix degradation.

Still another embodiment of the invention is a method of reducing extracellular matrix degradation. A cell is contacted with a reagent which specifically binds to a polynucleotide encoding a prostasin-like enzyme polypeptide or the product encoded by the polynucleotide, wherein the polynucleotide comprises a nucleotide sequence selected from the group consisting of:
nucleotide sequences which are at least about 50% identical to the nucleotide sequence shown in SEQ ID NO: 1 or SEQ ID NO: 5; and
the nucleotide sequence shown in SEQ ID NO: 1 or SEQ ID NO: 5.

Prostasin-like enzyme activity in the cell is thereby decreased.

The invention thus provides reagents and methods for regulating human prostasin-like enzyme activity which can be used inter alia, to suppress metastatic activity of malignant cells, to treat COPD and to enhance human prostasin-like enzyme activity during development.

BRIEF DESCRIPTION OF THE DRAWINGS

FIG. 1 shows the DNA-sequence encoding a prostasin-like enzyme polypeptide (SEQ ID NO:1).

FIG. 2 shows the amino acid sequence deduced from the DNA-sequence of FIG. 1 (SEQ ID NO:2).

FIG. 3 shows the amino acid sequence of the protein identified by Swiss Prot Accession No. Q16651 (SEQ ID NO:3).

FIG. 4 shows the DNA-sequence encoding a prostasin-like enzyme polypeptide (SEQ ID NO: 4).

FIG. 5 shows the DNA-sequence encoding a prostasin-like enzyme polypeptide (SEQ ID NO: 5).

FIG. 6 shows the amino acid sequence deduced from the DNA-sequence of FIG. 5 (SEQ ID NO: 6).

FIG. 7 shows the alignment of prostasin-like enzyme as shown in SEQ ID NO:2 with the human protein identified by Swiss Prot Accession No. Q16651 (SEQ ID NO:3).

FIG. 8 shows the prosite search results.

FIG. 9 shows the BLOCKS search results for SEQ ID NO:2.

FIG. 10 shows the BLAST alignment of SEQ ID NO:2 against swiss/Q16651/PSS8_HUMAN SEQ ID NO:3).

FIG. 11 shows the gene prediction for SEQ ID NO:1 based on EST BF689477 (SEQ ID NO:5)

FIG. 12 shows the relative expression of prostasin-like enzyme in various human tissues.

FIG. 13 shows the relative expression of prostasin-like enzyme in various human respiratory tissues and cells. Key: HBEC=cultured human bronchial epithelial cells; H441=Clara-like cells; SMC=cultured airway smooth muscle cells; SAE=cultured small airway epithelial cells; AII=primary cultured alveolar type II cells; PMN=polymorphonuclear leukocytes; Mono=monocytes; Cult. Mono=cultured monocytes (macrophage-like).

DETAILED DESCRIPTION OF THE INVENTION

The invention relates to an isolated polynucleotide encoding a prostasin-like enzyme polypeptide and being selected from the group consisting of:
1. a polynucleotide encoding a prostasin-like enzyme polypeptide comprising an amino acid sequence selected from the group consisting of:
   amino acid sequences which are at least about 50% identical to the amino acid sequence shown in SEQ ID NO: 2 or SEQ ID NO: 6; and the amino acid sequence shown in SEQ ID NO: 2 or SEQ ID NO: 6.
2. a polynucleotide comprising the sequence of SEQ ID NO: 1 or SEQ ID NO: 5;
3. a polynucleotide which hybridizes under stringent conditions to a polynucleotide specified in (a) and (b);
4. a polynucleotide the sequence of which deviates from the polynucleotide sequences specified in (a) to (c) due to the degeneration of the genetic code; and
5. a polynucleotide which represents a fragment, derivative or allelic variation of a polynucleotide sequence specified in (a) to (d).

Furthermore, it has been discovered by the present applicant that a novel prostasin-like enzyme, particularly a human prostasin-like enzyme, is a discovery of the present invention. Human prostasin-like enzyme as shown in SEQ ID NO:2 is 47% identical over 243 amino acids to the human protein identified by SwissProt Accession No. Q16651 (SEQ ID NO:3) and annotated as a prostasin precursor (FIG. 1). Prostasin is a trypsin-like serine protease which has been purified from human seminal fluid and is localized in epithelial cells and ducts of the prostate gland, as well as in colon, lung, kidney, pancreas, salivary gland, liver, and bronchi. (Yu et al., *J. Biol. Chem.* 269, 11843–48, 1994). Human prostasin-like enzyme contains a trypsin-serine and a trypsin-histidine region as shown in FIG. 1. Other domains identified in human prostasin-like enzyme include fibronectin domains, Kringle domains, and Apple domains, as shown in FIG. 3. Thus, human prostasin-like enzyme is believed to be useful for the same purposes as previously identified serine proteases, including prostasin. Regulation of human prostasin-like enzyme can be used, for example, to treat conditions such as osteoporosis, COPD, tumor metastasis, and neurodegenerative diseases.

Polypeptides

Human prostasin-like enzyme polypeptides according to the invention comprise at least 6, 10, 15, 25, 50, 75, 100, 125, 150, 175, 200, 225, 250, or 260 contiguous amino acids selected from the amino acid sequence shown in SEQ ID NO:2 or SEQ ID NO: 6 or a biologically active variant thereof, as defined below. A human prostasin-like enzyme polypeptide of the invention therefore can be a portion of a human prostasin-like enzyme protein, a full-length human prostasin-like enzyme protein, or a fusion protein comprising all or a portion of a human prostasin-like enzyme protein.

Biologically Active Variants

Human prostasin-like enzyme polypeptide variants which are biologically active, e.g., retain a serine protease activity, also are human prostasin-like enzyme polypeptides. Preferably, naturally or non-naturally occurring prostasin-like enzyme polypeptide variants have amino acid sequences which are at least about 50, 55, 60, 65, or 70, preferably about 75, 80, 85, 90, 96, 96, or 98% identical to the amino acid sequence shown in SEQ ID NO:2 or SEQ ID NO: 6 or a fragment thereof. Percent identity between a putative human prostasin-like enzyme polypeptide variant and an amino acid sequence of SEQ ID NO:2 or SEQ ID NO: 6 is determined using the Blast2 alignment program (Blosum62, Expect 10, standard genetic codes).

Variations in percent identity can be due, for example, to amino acid substitutions, insertions, or deletions. Amino acid substitutions are defined as one for one amino acid replacements. They are conservative in nature when the substituted amino acid has similar structural and/or chemical properties. Examples of conservative replacements are substitution of a leucine with an isoleucine or valine, an aspartate with a glutamate, or a threonine with a serine.

Amino acid insertions or deletions are changes to or within an amino acid sequence. They typically fall in the range of about 1 to 5 amino acids. Guidance in determining which amino acid residues can be substituted, inserted, or deleted without abolishing biological or immunological activity of a human prostasin-like enzyme polypeptide can be found using computer programs well known in the art, such as DNASTAR software. Whether an amino acid change results in a biologically active human prostasin-like enzyme polypeptide can readily be determined by assaying for serine protease activity, as described for example, in the specific Examples, below.

Fusion Proteins

Fusion proteins are useful for generating antibodies against human prostasin-like enzyme polypeptide amino acid sequences and for use in various assay systems. For example, fusion proteins can be used to identify proteins which interact with portions of a human prostasin-like enzyme polypeptide. Protein affinity chromatography or library-based assays for protein-protein interactions, such as the yeast two-hybrid or phage display systems, can be used for this purpose. Such methods are well known in the art and also can be used as drug screens.

A human prostasin-like enzyme polypeptide fusion protein comprises two polypeptide segments fused together by means of a peptide bond. The first polypeptide segment comprises at least 6, 10, 15, 25, 50, 75, 100, 125, 150, 175, 200, 225, 250, or 260 contiguous amino acids of SEQ ID NO:2 or SEQ ID NO: 6 or of a biologically active variant, such as those described above. The first polypeptide segment also can comprise full-length human prostasin-like human prostasin-like enzyme protein.

The second polypeptide segment can be a full-length protein or a protein fragment. Proteins commonly used in fusion protein construction include β-galactosidase, β-glucuronidase, green fluorescent protein (GFP), autofluorescent proteins, including blue fluorescent protein (BFP), glutathione-S-transferase (GST), luciferase, horse-radish peroxidase (and chloramphenicol acetyltransferase (CAT). Additionally, epitope tags are used in fusion protein constructions, including histidine (His) tags, FLAG tags, influenza hemagglutinin (HA) tags, Myc tags, VSV-G tags, and thioredoxin (Trx) tags. Other fusion constructions can include maltose binding protein (MBP), S-tag, Lex a DNA binding domain (DBD) fusions, GAL4 DNA binding domain fusions, and herpes simplex virus (HSV) BP16 protein fusions. A fusion protein also can be engineered to contain a cleavage site located between the human prostasin-like enzyme polypeptide-encoding sequence and the heterologous protein sequence, so that the human prostasin-like enzyme polypeptide can be cleaved and purified away from the heterologous moiety.

A fusion protein can be synthesized chemically, as is known in the art. Preferably, a fusion protein is produced by covalently linking two polypeptide segments or by standard procedures in the art of molecular biology. Recombinant DNA methods can be used to prepare fusion proteins, for example, by making a DNA construct which comprises coding sequences selected from SEQ ID NO:1 or SEQ ID NO: 5 in proper reading frame with nucleotides encoding the second polypeptide segment and expressing the DNA construct in a host cell, as is known in the art. Many kits for constructing fusion proteins are available from companies such as Promega Corporation (Madison, Wis.), Stratagene (La Jolla, Calif.), CLONTECH (Mountain View, Calif.), Santa Cruz Biotechnology (Santa Cruz, Calif.), MBL International Corporation (MIC; Watertown, Mass.), and Quantum Biotechnologies (Montreal, Canada; 1-888-DNA-KITS).

Identification of Species Homologs

Species homologs of human prostasin-like enzyme polypeptide can be obtained using human prostasin-like enzyme polypeptide polynucleotides (described below) to make suitable probes or primers for screening cDNA expression libraries from other species, such as mice, monkeys, or yeast, identifying cDNAs which encode homologs of human prostasin-like enzyme polypeptide, and expressing the cDNAs as is known in the art.

Polynucleotides

A human prostasin-like enzyme polynucleotide can be single- or double-stranded and comprises a coding sequence or the complement of a coding sequence for a human prostasin-like enzyme polypeptide. A full-length coding sequence for human prostasin-like enzyme is shown in SEQ ID NO:1 and SEQ ID NO: 5.

Degenerate nucleotide sequences encoding human prostasin-like enzyme polypeptides, as well as homologous nucleotide sequences which are at least about 50, preferably about 75, 90, 96, or 98% identical to the nucleotide sequence shown in SEQ ID NO:1 or SEQ ID NO: 5 also are human prostasin-like enzyme polynucleotides. Percent sequence identity between the sequences of two polynucleotides is determined using computer programs such as ALIGN which employ the FASTA algorithm, using an affine gap search with a gap open penalty of −12 and a gap extension penalty of −2. Complementary DNA (cDNA) molecules, species homologs, and variants of human prostasin-like enzyme polypeptides also are human prostasin-like enzyme polynucleotides.

Identification of Polynucleotide Variants and Homologs

Variants and homologs of the human prostasin-like enzyme polynucleotides described above also are human prostasin-like enzyme polynucleotides. Typically, homologous human prostasin-like enzyme polynucleotide sequences can be identified by hybridization of candidate polynucleotides to known human prostasin-like enzyme polynucleotides under stringent conditions, as is known in the art. For example, using the following wash conditions—2×SSC (0.3 M NaCl, 0.03 M sodium citrate, pH 7.0), 0.1% SDS, room temperature twice, 30 minutes each; then 2×SSC, 0.1% SDS, 50° C. once, 30 minutes; then 2×SSC, room temperature twice, 10 minutes each—homologous sequences can be identified which contain at most about 25–30% basepair mismatches. More preferably, homologous nucleic acid strands contain 15–25% basepair mismatches, even more preferably 5–15% basepair mismatches.

Species homologs of the human prostasin-like enzyme polynucleotides disclosed herein also can be identified by making suitable probes or primers and screening cDNA expression libraries from other species, such as mice, monkeys, or yeast. Human variants of human prostasin-like enzyme polynucleotides can be identified, for example, by screening human cDNA expression libraries. It is well known that the $T_m$ of a double-stranded DNA decreases by 1–1.5° C. with every 1% decrease in homology (Bonner et al., *J. Mol. Biol.* 81, 123 (1973). Variants of human prostasin-like enzyme polynucleotides or human prostasin-like enzyme polynucleotides of other species can therefore be identified by hybridizing a putative homologous human prostasin-like enzyme polynucleotide with a polynucleotide having a nucleotide sequence of SEQ ID NO:1 or SEQ ID NO: 5 or the complement thereof to form a test hybrid. The melting temperature of the test hybrid is compared with the melting temperature of a hybrid comprising polynucleotides having perfectly complementary nucleotide sequences, and the number or percent of basepair mismatches within the test hybrid is calculated.

Nucleotide sequences which hybridize to human prostasin-like enzyme polynucleotides or their complements following stringent hybridization and/or wash conditions also are human prostasin-like enzyme polynucleotides. Stringent wash conditions are well known and understood in the art and are disclosed, for example, in Sambrook et al., MOLECULAR CLONING: A LABORATORY MANUAL, 2d ed., 1989, at pages 9.50–9.51.

Typically, for stringent hybridization conditions a combination of temperature and salt concentration should be chosen that is approximately 12–20° C. below the calculated $T_m$ of the hybrid under study. The $T_m$ of a hybrid between a human prostasin-like enzyme polynucleotide having a nucleotide sequence shown in SEQ ID NO:1 or SEQ ID NO: 5 or the complement thereof and a polynucleotide sequence which is at least about 50, preferably about 75, 90, 96, or 98% identical to one of those nucleotide sequences can be calculated, for example, using the equation of Bolton and McCarthy, *Proc. Natl. Acad. Sci. U.S.A.* 48, 1390 (1962):

$$T_m = 81.5° C. - 16.6(\log_{10}[Na^+]) + 0.41(\% G+C) - 0.63(\% \text{ formamide}) - 600/l,$$

where l=the length of the hybrid in basepairs.

Stringent wash conditions include, for example, 4×SSC at 65° C., or 50% formamide, 4×SSC at 42° C., or 0.5×SSC, 0.1% SDS at 65° C. Highly stringent wash conditions include, for example, 0.2×SSC at 65° C.

Preparation of Polynucleotides

A naturally occurring human prostasin-like enzyme polynucleotide can be isolated free of other cellular components such as membrane components, proteins, and lipids. Polynucleotides can be made by a cell and isolated using standard nucleic acid purification techniques, or synthesized using an amplification technique, such as the polymerase chain reaction (PCR), or by using an automatic synthesizer. Methods for isolating polynucleotides are routine and are known in the art. Any such technique for obtaining a polynucleotide can be used to obtain isolated human prostasin-like enzyme polynucleotides. For example, restriction enzymes and probes can be used to isolate polynucleotide fragments which comprises human prostasin-like enzyme nucleotide sequences. Isolated polynucleotides are in preparations which are free or at least 70, 80, or 90% free of other molecules.

Human prostasin-like enzyme cDNA molecules can be made with standard molecular biology techniques, using human prostasin-like enzyme mRNA as a template. human prostasin-like enzyme cDNA molecules can thereafter be replicated using molecular biology techniques known in the art and disclosed in manuals such as Sambrook et al. (1989). An amplification technique, such as PCR, can be used to obtain additional copies of polynucleotides of the invention, using either human genomic DNA or cDNA as a template.

Alternatively, synthetic chemistry techniques can be used to synthesizes human prostasin-like enzyme polynucleotides. The degeneracy of the genetic code allows alternate nucleotide sequences to be synthesized which will encode a human prostasin-like enzyme polypeptide having, for example, an amino acid sequence shown in SEQ ID NO:2 or SEQ ID NO: 6 or a biologically active variant thereof.

Extending Polynucleotides

Various PCR-based methods can be used to extend the nucleic acid sequences disclosed herein to detect upstream sequences such as promoters and regulatory elements. For example, restriction-site PCR uses universal primers to retrieve unknown sequence adjacent to a known locus (Sarkar, *PCR Methods Applic.* 2, 318–322, 1993). Genomic DNA is first amplified in the presence of a primer to a linker sequence and a primer specific to the known region. The amplified sequences are then subjected to a second round of PCR with the same linker primer and another specific primer internal to the first one. Products of each round of PCR are transcribed with an appropriate RNA polymerase and sequenced using reverse transcriptase.

Inverse PCR also can be used to amplify or extend sequences using divergent primers based on a known region (Triglia et al., *Nucleic Acids Res.* 16, 8186, 1988). Primers can be designed using commercially available software, such as OLIGO 4.06 Primer Analysis software (National Biosciences Inc., Plymouth, Minn.), to be 22–30 nucleotides in length, to have a GC content of 50% or more, and to anneal to the target sequence at temperatures about 68–72° C. The method uses several restriction enzymes to generate a suitable fragment in the known region of a gene. The fragment is then circularized by intramolecular ligation and used as a PCR template.

Another method which can be used is capture PCR, which involves PCR amplification of DNA fragments adjacent to a known sequence in human and yeast artificial chromosome DNA (Lagerstrom et al., *PCR Methods Applic.* 1, 111–119, 1991). In this method, multiple restriction enzyme digestions and ligations also can be used to place an engineered double-stranded sequence into an unknown fragment of the DNA molecule before performing PCR.

Another method which can be used to retrieve unknown sequences is that of Parker et al., *Nucleic Acids Res.* 19, 3055–3060, 1991). Additionally, PCR, nested primers, and PROMOTERFINDER libraries (CLONTECH, Palo Alto, Calif.) can be used to walk genomic DNA (CLONTECH, Palo Alto, Calif.). This process avoids the need to screen libraries and is useful in finding intron/exon junctions.

When screening for full-length cDNAs, it is preferable to use libraries that have been size-selected to include larger cDNAs. Randomly-primed libraries are preferable, in that they will contain more sequences which contain the 5' regions of genes. Use of a randomly primed library may be especially preferable for situations in which an oligo d(T) library does not yield a full-length cDNA. Genomic libraries can be useful for extension of sequence into 5' non-transcribed regulatory regions.

Commercially available capillary electrophoresis systems can be used to analyze the size or confirm the nucleotide sequence of PCR or sequencing products. For example, capillary sequencing can employ flowable polymers for electrophoretic separation, four different fluorescent dyes (one for each nucleotide) which are laser activated, and detection of the emitted wavelengths by a charge coupled device camera. Output/light intensity can be converted to electrical signal using appropriate software (e.g. GENOTYPER and Sequence NAVIGATOR, Perkin Elmer), and the entire process from loading of samples to computer analysis and electronic data display can be computer controlled. Capillary electrophoresis is especially preferable for the sequencing of small pieces of DNA which might be present in limited amounts in a particular sample.

Obtaining Polypeptides

Human prostasin-like enzyme polypeptides can be obtained, for example, by purification from human cells, by expression of human prostasin-like enzyme polynucleotides, or by direct chemical synthesis.

Protein Purification

Human prostasin-like enzyme polypeptides can be purified from any cell which expresses the enzyme, including host cells which have been transfected with human prostasin-like enzyme expression constructs. Human fetal heart provides an especially useful source of human prostasin-like enzyme polypeptides. A purified human prostasin-like enzyme polypeptide is separated from other compounds which normally associate with the human prostasin-like enzyme polypeptide in the cell, such as certain proteins, carbohydrates, or lipids, using methods well-known in the art. Such methods include, but are not limited to, size exclusion chromatography, ammonium sulfate fractionation, ion exchange chromatography, affinity chromatography, and preparative gel electrophoresis. A preparation of purified human prostasin-like enzyme polypeptides is at least 80% pure; preferably, the preparations are 90%, 95%, or 99% pure. Purity of the preparations can be assessed by any means known in the art, such as SDS-polyacrylamide gel electrophoresis.

Expression of Polynucleotides

To express a human prostasin-like enzyme polynucleotide, the polynucleotide can be inserted into an expression vector which contains the necessary elements for the transcription and translation of the inserted coding sequence. Methods which are well known to those skilled in the art can be used to construct expression vectors containing sequences encoding human prostasin-like enzyme polypeptides and appropriate transcriptional and translational control elements. These methods include in vitro recombinant DNA techniques, synthetic techniques, and in vivo genetic recombination. Such techniques are described, for example, in Sambrook et al. (1989) and in Ausubel et al., CURRENT PROTOCOLS IN MOLECULAR BIOLOGY, John Wiley & Sons, New York, N.Y., 1989.

A variety of expression vector/host systems can be utilized to contain and express sequences encoding a human prostasin-like enzyme polypeptide. These include, but are not limited to, microorganisms, such as bacteria transformed with recombinant bacteriophage, plasmid, or cosmid DNA expression vectors; yeast transformed with yeast expression vectors, insect cell systems infected with virus expression vectors (e.g., baculovirus), plant cell systems transformed with virus expression vectors (e.g., cauliflower mosaic virus, CaMV; tobacco mosaic virus, TMV) or with bacterial expression vectors (e.g., Ti or pBR322 plasmids), or animal cell systems.

The control elements or regulatory sequences are those non-translated regions of the vector—enhancers, promoters, 5' and 3' untranslated regions—which interact with host cellular proteins to carry out transcription and translation. Such elements can vary in their strength and specificity. Depending on the vector system and host utilized, any number of suitable transcription and translation elements, including constitutive and inducible promoters, can be used. For example, when cloning in bacterial systems, inducible promoters such as the hybrid lacZ promoter of the BLUESCRIPT phagemid (Stratagene, LaJolla, Calif.) or pSPORT1 plasmid (Life Technologies) and the like can be used. The baculovirus polyhedrin promoter can be used in insect cells. Promoters or enhancers derived from the genomes of plant cells (e.g., heat shock, RUBISCO, and storage protein genes) or from plant viruses (e.g., viral promoters or leader sequences) can be cloned into the vector. In mammalian cell systems, promoters from mammalian genes or from mammalian viruses are preferable. If it is necessary to generate a cell line that contains multiple copies of a nucleotide sequence encoding a human prostasin-like enzyme polypeptide, vectors based on SV40 or EBV can be used with an appropriate selectable marker.

Bacterial and Yeast Expression Systems

In bacterial systems, a number of expression vectors can be selected depending upon the use intended for the human prostasin-like enzyme polypeptide. For example, when a large quantity of a human prostasin-like enzyme polypeptide is needed for the induction of antibodies, vectors which direct high level expression of fusion proteins that are readily purified can be used. Such vectors include, but are not limited to, multifunctional E. coli cloning and expression vectors such as BLUESCRIPT (Stratagene). In a BLUESCRIPT vector, a sequence encoding the human prostasin-like enzyme polypeptide can be ligated into the vector in frame with sequences for the amino-terminal Met and the subsequent 7 residues of β-galactosidase so that a hybrid protein is produced. pIN vectors (Van Heeke & Schuster, J. Biol. Chem. 264, 5503–5509, 1989) or pGEX vectors (Promega, Madison, Wis.) also can be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. Proteins made in such systems can be designed to include heparin, thrombin, or factor Xa protease cleavage sites so that the cloned polypeptide of interest can be released from the GST moiety at will.

In the yeast Saccharomyces cerevisiae, a number of vectors containing constitutive or inducible promoters such as alpha factor, alcohol oxidase, and PGH can be used. For reviews, see Ausubel et al. (1989) and Grant et al., Methods Enzymol. 153, 516–544, 1987.

Plant and Insect Expression Systems

If plant expression vectors are used, the expression of sequences encoding human prostasin-like enzyme polypeptides can be driven by any of a number of promoters. For example, viral promoters such as the 35S and 19S promoters of CaMV can be used alone or in combination with the omega leader sequence from TMV (Takamatsu, EMBO J. 6, 307–311, 1987). Alternatively, plant promoters such as the small subunit of RUBISCO or heat shock promoters can be used (Coruzzi et al., EMBO J. 3, 1671–1680, 1984; Broglie et al., Science 224, 838–843, 1984; Winter et al., Results Probl. Cell Differ. 17, 85–105, 1991). These constructs can be introduced into plant cells by direct DNA transformation or by pathogen-mediated transfection. Such techniques are described in a number of generally available reviews (e.g., Hobbs or Murray, in MCGRAW HILL YEARBOOK OF SCIENCE AND TECHNOLOGY, McGraw Hill, New York, N.Y., pp. 191–196, 1992).

An insect system also can be used to express a human prostasin-like enzyme polypeptide. For example, in one such system Autographa californica nuclear polyhedrosis virus (AcNPV) is used as a vector to express foreign genes in Spodoptera frugiperda cells or in Trichoplusia larvae. Sequences encoding human prostasin-like enzyme polypeptides can be cloned into a non-essential region of the virus, such as the polyhedrin gene, and placed under control of the polyhedrin promoter. Successful insertion of human prostasin-like enzyme polypeptides will render the polyhedrin gene inactive and produce recombinant virus lacking coat protein. The recombinant viruses can then be used to infect S. frugiperda cells or Trichoplusia larvae in which human prostasin-like enzyme polypeptides can be expressed (Engelhard et al., Proc. Nat. Acad. Sci. 91, 3224–3227, 1994).

Mammalian Expression Systems

A number of viral-based expression systems can be used to express human prostasin-like enzyme polypeptides in mammalian host cells. For example, if an adenovirus is used as an expression vector, sequences encoding human prostasin-like enzyme polypeptides can be ligated into an adenovirus transcription/translation complex comprising the late promoter and tripartite leader sequence. Insertion in a non-essential E1 or E3 region of the viral genome can be used to obtain a viable virus which is capable of expressing a human prostasin-like enzyme polypeptide in infected host cells (Logan & Shenk, Proc. Natl. Acad. Sci. 81, 3655–3659, 1984). If desired, transcription enhancers, such as the Rous sarcoma virus (RSV) enhancer, can be used to increase expression in mammalian host cells.

Human artificial chromosomes (HACs) also can be used to deliver larger fragments of DNA than can be contained and expressed in a plasmid. HACs of 6M to 10M are constructed and delivered to cells via conventional delivery methods (e.g., liposomes, polycationic amino polymers, or vesicles).

Specific initiation signals also can be used to achieve more efficient translation of sequences encoding human prostasin-like enzyme polypeptides. Such signals include the ATG initiation codon and adjacent sequences. In cases where sequences encoding a human prostasin-like enzyme polypeptide, its initiation codon, and upstream sequences are inserted into the appropriate expression vector, no additional transcriptional or translational control signals may be needed. However, in cases where only coding sequence, or a fragment thereof, is inserted, exogenous translational control signals (including the ATG initiation codon) should be provided. The initiation codon should be in the correct reading frame to ensure translation of the entire insert. Exogenous translational elements and initiation codons can be of various origins, both natural and synthetic. The efficiency of expression can be enhanced by the inclusion of enhancers which are appropriate for the particular cell system which is used (see Scharf et al., *Results Probl. Cell Differ.* 20, 125–162, 1994).

Host Cells

A host cell strain can be chosen for its ability to modulate the expression of the inserted sequences or to process the expressed human prostasin-like enzyme polypeptide in the desired fashion. Such modifications of the polypeptide include, but are not limited to, acetylation, carboxylation, glycosylation, phosphorylation, lipidation, and acylation. Post-translational processing which cleaves a "prepro" form of the polypeptide also can be used to facilitate correct insertion, folding and/or function. Different host cells which have specific cellular machinery and characteristic mechanisms for post-translational activities (e.g., CHO, HeLa, MDCK, HEK293, and WI38), are available from the American Type Culture Collection (ATCC; 10801 University Boulevard, Manassas, Va. 20110–2209) and can be chosen to ensure the correct modification and processing of the foreign protein.

Stable expression is preferred for long-term, high-yield production of recombinant proteins. For example, cell lines which stably express human prostasin-like enzyme polypeptides can be transformed using expression vectors which can contain viral origins of replication and/or endogenous expression elements and a selectable marker gene on the same or on a separate vector. Following the introduction of the vector, cells can be allowed to grow for 1–2 days in an enriched medium before they are switched to a selective medium. The purpose of the selectable marker is to confer resistance to selection, and its presence allows growth and recovery of cells which successfully express the introduced human prostasin-like enzyme sequences. Resistant clones of stably transformed cells can be proliferated using tissue culture techniques appropriate to the cell type. See, for example, ANIMAL CELL CULTURE, R. I. Freshney, ed., 1986.

Any number of selection systems can be used to recover transformed cell lines. These include, but are not limited to, the herpes simplex virus thymidine kinase (Wigler et al., *Cell* 11, 223–32, 1977) and adenine phosphoribosyltransferase (Lowy et al., *Cell* 22, 817–23, 1980) genes which can be employed in tk$^-$ or aprt$^-$ cells, respectively. Also, antimetabolite, antibiotic, or herbicide resistance can be used as the basis for selection. For example, dhfr confers resistance to methotrexate (Wigler et al., *Proc. Natl. Acad. Sci.* 77, 3567–70, 1980), npt confers resistance to the aminoglycosides, neomycin and G-418 (Colbere-Garapin et al., *J. Mol. Biol.* 150, 1–14, 1981), and als and pat confer resistance to chlorsulfuron and phosphinotricin acetyltransferase, respectively (Murray, 1992, supra). Additional selectable genes have been described. For example, trpB allows cells to utilize indole in place of tryptophan, or hisD, which allows cells to utilize histinol in place of histidine (Hartman & Mulligan, *Proc. Natl. Acad. Sci.* 85, 8047–51, 1988). Visible markers such as anthocyanins, β-glucuronidase and its substrate GUS, and luciferase and its substrate luciferin, can be used to identify transformants and to quantify the amount of transient or stable protein expression attributable to a specific vector system (Rhodes et al., *Methods Mol. Biol.* 55, 121–131, 1995).

Detecting Expression

Although the presence of marker gene expression suggests that the human prostasin-like enzyme polynucleotide is also present, its presence and expression may need to be confirmed. For example, if a sequence encoding a human prostasin-like enzyme polypeptide is inserted within a marker gene sequence, transformed cells containing sequences which encode a human prostasin-like enzyme polypeptide can be identified by the absence of marker gene function. Alternatively, a marker gene can be placed in tandem with a sequence encoding a human prostasin-like enzyme polypeptide under the control of a single promoter. Expression of the marker gene in response to induction or selection usually indicates expression of the human prostasin-like enzyme polynucleotide.

Alternatively, host cells which contain a human prostasin-like enzyme polynucleotide and which express a human prostasin-like enzyme polypeptide can be identified by a variety of procedures known to those of skill in the art. These procedures include, but are not limited to, DNA-DNA or DNA-RNA hybridizations and protein bioassay or immunoassay techniques which include membrane, solution, or chip-based technologies for the detection and/or quantification of nucleic acid or protein. For example, the presence of a polynucleotide sequence encoding a human prostasin-like enzyme polypeptide can be detected by DNA-DNA or DNA-RNA hybridization or amplification using probes or fragments or fragments of polynucleotides encoding a human prostasin-like enzyme polypeptide. Nucleic acid amplification-based assays involve the use of oligonucleotides selected from sequences encoding a human prostasin-like enzyme polypeptide to detect transformants which contain a human prostasin-like enzyme polynucleotide.

A variety of protocols for detecting and measuring the expression of a human prostasin-like enzyme polypeptide, using either polyclonal or monoclonal antibodies specific for the polypeptide, are known in the art. Examples include enzyme-linked immunosorbent assay (ELISA), radioimmunoassay (RIA), and fluorescence activated cell sorting (FACS). A two-site, monoclonal-based immunoassay using monoclonal antibodies reactive to two non-interfering epitopes on a human prostasin-like enzyme polypeptide can be used, or a competitive binding assay can be employed. These and other assays are described in Hampton et al., SEROLOGICAL METHODS: A LABORATORY MANUAL, APS Press, St. Paul, Minn., 1990) and Maddox et al., *J. Exp. Med.* 158, 1211–1216, 1983).

A wide variety of labels and conjugation techniques are known by those skilled in the art and can be used in various nucleic acid and amino acid assays. Means for producing labeled hybridization or PCR probes for detecting sequences related to polynucleotides encoding human prostasin-like enzyme polypeptides include oligolabeling, nick translation, end-labeling, or PCR amplification using a labeled nucleotide. Alternatively, sequences encoding a human prostasin-like enzyme polypeptide can be cloned into a vector for the production of an mRNA probe. Such vectors are known in the art, are commercially available, and can be used to synthesize RNA probes in vitro by addition of labeled nucleotides and an appropriate RNA polymerase such as T7, T3, or SP6. These procedures can be conducted using a variety of commercially available kits (Amersham Pharmacia Biotech, Promega, and US Biochemical). Suitable reporter molecules or labels which can be used for ease of detection include radionuclides, enzymes, and fluorescent, chemiluminescent, or chromogenic agents, as well as substrates, cofactors, inhibitors, magnetic particles, and the like.

Expression and Purification of Polypeptides

Host cells transformed with nucleotide sequences encoding a human prostasin-like enzyme polypeptide can be cultured under conditions suitable for the expression and recovery of the protein from cell culture. The polypeptide produced by a transformed cell can be secreted or contained intracellularly depending on the sequence and/or the vector used. As will be understood by those of skill in the art, expression vectors containing polynucleotides which encode human prostasin-like enzyme polypeptides can be designed to contain signal sequences which direct secretion of soluble human prostasin-like enzyme polypeptides through a prokaryotic or eukaryotic cell membrane or which direct the membrane insertion of membrane-bound human prostasin-like enzyme polypeptide.

As discussed above, other constructions can be used to join a sequence encoding a human prostasin-like enzyme polypeptide to a nucleotide sequence encoding a polypeptide domain which will facilitate purification of soluble proteins. Such purification facilitating domains include, but are not limited to, metal chelating peptides such as histidine-tryptophan modules that allow purification on immobilized metals, protein A domains that allow purification on immobilized immunoglobulin, and the domain utilized in the FLAGS extension/affinity purification system (Immunex Corp., Seattle, Wash.). Inclusion of cleavable linker sequences such as those specific for Factor Xa or enterokinase (Invitrogen, San Diego, Calif.) between the purification domain and the human prostasin-like enzyme polypeptide also can be used to facilitate purification. One such expression vector provides for expression of a fusion protein containing a human prostasin-like enzyme polypeptide and 6 histidine residues preceding a thioredoxin or an enterokinase cleavage site. The histidine residues facilitate purification by IMAC (immobilized metal ion affinity chromatography, as described in Porath et al., Prot. Exp. Purif. 3, 263–281, 1992), while the enterokinase cleavage site provides a means for purifying the human prostasin-like enzyme polypeptide from the fusion protein. Vectors which contain fusion proteins are disclosed in Kroll et al., DNA Cell Biol. 12, 441–453, 1993.

Chemical Synthesis

Sequences encoding a human prostasin-like enzyme polypeptide can be synthesized, in whole or in part, using chemical methods well known in the art (see Caruthers et al., Nucl. Acids Res. Symp. Ser. 215–223, 1980; Horn et al. Nucl. Acids Res. Symp. Ser. 225–232, 1980). Alternatively, a human prostasin-like enzyme polypeptide itself can be produced using chemical methods to synthesize its amino acid sequence, such as by direct peptide synthesis using solid-phase techniques (Merrifield, J. Am. Chem. Soc. 85, 2149–2154, 1963; Roberge et al., Science 269, 202–204, 1995). Protein synthesis can be performed using manual techniques or by automation. Automated synthesis can be achieved, for example, using Applied Biosystems 431A Peptide Synthesizer (Perkin Elmer). Optionally, fragments of human prostasin-like enzyme polypeptides can be separately synthesized and combined using chemical methods to produce a full-length molecule.

The newly synthesized peptide can be substantially purified by preparative high performance liquid chromatography (e.g., Creighton, PROTEINS: STRUCTURES AND MOLECULAR PRINCIPLES, WH Freeman and Co., New York, N.Y., 1983). The composition of a synthetic human prostasin-like enzyme polypeptide can be confirmed by amino acid analysis or sequencing (e.g., the Edman degradation procedure; see Creighton, supra). Additionally, any portion of the amino acid sequence of the human prostasin-like enzyme polypeptide can be altered during direct synthesis and/or combined using chemical methods with sequences from other proteins to produce a variant polypeptide or a fusion protein.

Production of Altered Polypeptides

As will be understood by those of skill in the art, it may be advantageous to produce human prostasin-like enzyme polypeptide-encoding nucleotide sequences possessing non-naturally occurring codons. For example, codons preferred by a particular prokaryotic or eukaryotic host can be selected to increase the rate of protein expression or to produce an RNA transcript having desirable properties, such as a half-life which is longer than that of a transcript generated from the naturally occurring sequence.

The nucleotide sequences disclosed herein can be engineered using methods generally known in the art to alter human prostasin-like enzyme polypeptide-encoding sequences for a variety of reasons, including but not limited to, alterations which modify the cloning, processing, and/or expression of the polypeptide or mRNA product. DNA shuffling by random fragmentation and PCR reassembly of gene fragments and synthetic oligonucleotides can be used to engineer the nucleotide sequences. For example, site-directed mutagenesis can be used to insert new restriction sites, alter glycosylation patterns, change codon preference, produce splice variants, introduce mutations, and so forth.

Antibodies

Any type of antibody known in the art can be generated to bind specifically to an epitope of a human prostasin-like enzyme polypeptide. "Antibody" as used herein includes intact immunoglobulin molecules, as well as fragments thereof, such as Fab, $F(ab')_2$, and Fv, which are capable of binding an epitope of a human prostasin-like enzyme polypeptide. Typically, at least 6, 8, 10, or 12 contiguous amino acids are required to form an epitope. However, epitopes which involve non-contiguous amino acids may require more, e.g., at least 15, 25, or 50 amino acids.

An antibody which specifically binds to an epitope of a human prostasin-like enzyme polypeptide can be used therapeutically, as well as in immunochemical assays, such as Western blots, ELISAs, radioimmunoassays, immunohistochemical assays, immunoprecipitations, or other immunochemical assays known in the art. Various immunoassays can be used to identify antibodies having the desired specificity. Numerous protocols for competitive binding or immunoradiometric assays are well known in the art. Such immunoassays typically involve the measurement of complex formation between an immunogen and an antibody which specifically binds to the immunogen.

Typically, an antibody which specifically binds to a human prostasin-like enzyme polypeptide provides a detection signal at least 5-, 10-, or 20-fold higher than a detection signal provided with other proteins when used in an immunochemical assay. Preferably, antibodies which specifically bind to human prostasin-like enzyme polypeptides do not detect other proteins in immunochemical assays and can immunoprecipitate a human prostasin-like enzyme polypeptide from solution.

Human prostasin-like enzyme polypeptides can be used to immunize a mammal, such as a mouse, rat, rabbit, guinea pig, monkey, or human, to produce polyclonal antibodies. If desired, a human prostasin-like enzyme polypeptide can be conjugated to a carrier protein, such as bovine serum albumin, thyroglobulin, and keyhole limpet hemocyanin. Depending on the host species, various adjuvants can be used to increase the immunological response. Such adjuvants include, but are not limited to, Freund's adjuvant, mineral gels (e.g., aluminum hydroxide), and surface active substances (e.g. lysolecithin, pluronic polyols, polyanions, peptides, oil emulsions, keyhole limpet hemocyanin, and dinitrophenol). Among adjuvants used in humans, BCG (bacilli Calmette-Guerin) and *Corynebacterium parvum* are especially useful.

Monoclonal antibodies which specifically bind to a human prostasin-like enzyme polypeptide can be prepared using any technique which provides for the production of antibody molecules by continuous cell lines in culture. These techniques include, but are not limited to, the hybridoma technique, the human B-cell hybridoma technique, and the EBV-hybridoma technique (Kohler et al., *Nature* 256, 495–497, 1985; Kozbor et al., *J. Immunol. Methods* 81, 31–42, 1985; Cote et al., *Proc. Natl. Acad. Sci.* 80, 2026–2030, 1983; Cole et al., *Mol. Cell Biol.* 62, 109–120, 1984).

In addition, techniques developed for the production of "chimeric antibodies," the splicing of mouse antibody genes to human antibody genes to obtain a molecule with appropriate antigen specificity and biological activity, can be used (Morrison et al., *Proc. Natl. Acad. Sci.* 81, 6851–6855, 1984; Neuberger et al., *Nature* 312, 604–608, 1984; Takeda et al., *Nature* 314, 452–454, 1985). Monoclonal and other antibodies also can be "humanized" to prevent a patient from mounting an immune response against the antibody when it is used therapeutically. Such antibodies may be sufficiently similar in sequence to human antibodies to be used directly in therapy or may require alteration of a few key residues. Sequence differences between rodent antibodies and human sequences can be minimized by replacing residues which differ from those in the human sequences by site directed mutagenesis of individual residues or by grating of entire complementarity determining regions. Alternatively, humanized antibodies can be produced using recombinant methods, as described in GB2188638B. Antibodies which specifically bind to a human prostasin-like enzyme polypeptide can contain antigen binding sites which are either partially or fully humanized, as disclosed in U.S. Pat. No. 5,565,332.

Alternatively, techniques described for the production of single chain antibodies can be adapted using methods known in the art to produce single chain antibodies which specifically bind to human prostasin-like enzyme polypeptides. Antibodies with related specificity, but of distinct idiotypic composition, can be generated by chain shuffling from random combinatorial immunoglobin libraries (Burton, *Proc. Natl. Acad. Sci.* 88, 11120–23, 1991).

Single-chain antibodies also can be constructed using a DNA amplification method, such as PCR, using hybridoma cDNA as a template (Thirion et al., 1996, *Eur. J. Cancer Prev.* 5, 507–11). Single-chain antibodies can be mono- or bispecific, and can be bivalent or tetravalent. Construction of tetravalent, bispecific single-chain antibodies is taught, for example, in Coloma & Morrison, 1997, *Nat. Biotechnol.* 15, 159–63. Construction of bivalent, bispecific single-chain antibodies is taught in Mallender & Voss, 1994, *J. Biol. Chem.* 269, 199–206.

A nucleotide sequence encoding a single-chain antibody can be constructed using manual or automated nucleotide synthesis, cloned into an expression construct using standard recombinant DNA methods, and introduced into a cell to express the coding sequence, as described below. Alternatively, single-chain antibodies can be produced directly using, for example, filamentous phage technology (Verhaar et al., 1995, *Int. J. Cancer* 61, 497–501; Nicholls et al., 1993, *J. Immunol. Meth.* 165, 81–91).

Antibodies which specifically bind to human prostasin-like enzyme polypeptides also can be produced by inducing in vivo production in the lymphocyte population or by screening immunoglobulin libraries or panels of highly specific binding reagents as disclosed in the literature (Orlandi et al., *Proc. Natl. Acad. Sci.* 86, 3833–3837, 1989; Winter et al., *Nature* 349, 293–299, 1991).

Other types of antibodies can be constructed and used therapeutically in methods of the invention. For example, chimeric antibodies can be constructed as disclosed in WO 93/03151. Binding proteins which are derived from immunoglobulins and which are multivalent and multispecific, such as the "diabodies" described in WO 94/13804, also can be prepared.

Antibodies according to the invention can be purified by methods well known in the art. For example, antibodies can be affinity purified by passage over a column to which a human prostasin-like enzyme polypeptide is bound. The bound antibodies can then be eluted from the column using a buffer with a high salt concentration.

Antisense Oligonucleotides

Antisense oligonucleotides are nucleotide sequences which are complementary to a specific DNA or RNA sequence. Once introduced into a cell, the complementary nucleotides combine with natural sequences produced by the cell to form complexes and block either transcription or translation. Preferably, an antisense oligonucleotide is at least 11 nucleotides in length, but can be at least 12, 15, 20, 25, 30, 35, 40, 45, or 50 or more nucleotides long. Longer sequences also can be used. Antisense oligonucleotide molecules can be provided in a DNA construct and introduced into a cell as described above to decrease the level of human prostasin-like enzyme gene products in the cell.

Antisense oligonucleotides can be deoxyribonucleotides, ribonucleotides, or a combination of both. Oligonucleotides can be synthesized manually or by an automated synthesizer, by covalently linking the 5' end of one nucleotide with the 3' end of another nucleotide with non-phosphodiester internucleotide linkages such alkylphosphonates, phosphorothioates, phosphorodithioates, alkylphosphonothioates, alkylphosphonates, phosphoramidates, phosphate esters, carbamates, acetamidate, carboxymethyl esters, carbonates, and phosphate triesters. See Brown, *Meth. Mol. Biol.* 20, 1–8, 1994; Sonveaux, *Meth. Mol. Biol.* 26, 1–72, 1994; Uhlmann et al., *Chem. Rev.* 90, 543–583, 1990.

Modifications of human prostasin-like enzyme gene expression can be obtained by designing antisense oligonucleotides which will form duplexes to the control, 5', or regulatory regions of the human prostasin-like enzyme gene. Oligonucleotides derived from the transcription initiation site, e.g., between positions −10 and +10 from the start site, are preferred. Similarly, inhibition can be achieved using "triple helix" base-pairing methodology. Triple helix pairing is useful because it causes inhibition of the ability of the double helix to open sufficiently for the binding of polymerases, transcription factors, or chaperons. Therapeutic advances using triplex DNA have been described in the literature (e.g., Gee et al., in Huber & Carr, MOLECULAR AND IMMUNOLOGIC APPROACHES, Futura Publishing Co., Mt. Kisco, N.Y., 1994). An antisense oligonucleotide also can be designed to block translation of mRNA by preventing the transcript from binding to ribosomes.

Precise complementarity is not required for successful complex formation between an antisense oligonucleotide and the complementary sequence of a human prostasin-like enzyme polynucleotide. Antisense oligonucleotides which comprise, for example, 2, 3, 4, or 5 or more stretches of contiguous nucleotides which are precisely complementary to a human prostasin-like enzyme polynucleotide, each separated by a stretch of contiguous nucleotides which are not complementary to adjacent human prostasin-like enzyme nucleotides, can provide sufficient targeting specificity for human prostasin-like enzyme mRNA. Preferably, each stretch of complementary contiguous nucleotides is at least 4, 5, 6, 7, or 8 or more nucleotides in length. Non-complementary intervening sequences are preferably 1, 2, 3, or 4 nucleotides in length. One skilled in the art can easily use the calculated melting point of an antisense-sense pair to determine the degree of mismatching which will be tolerated between a particular antisense oligonucleotide and a particular human prostasin-like enzyme polynucleotide sequence.

Antisense oligonucleotides can be modified without affecting their ability to hybridize to a human prostasin-like enzyme polynucleotide. These modifications can be internal or at one or both ends of the antisense molecule. For example, internucleoside phosphate linkages can be modified by adding cholesteryl or diamine moieties with varying numbers of carbon residues between the amino groups and terminal ribose. Modified bases and/or sugars, such as arabinose instead of ribose, or a 3',5'-substituted oligonucleotide in which the 3' hydroxyl group or the 5' phosphate group are substituted, also can be employed in a modified antisense oligonucleotide. These modified oligonucleotides can be prepared by methods well known in the art. See, e.g., Agrawal et al., *Trends Biotechnol.* 10, 152–158, 1992; Uhlmann et al., *Chem. Rev.* 90, 543–584, 1990; Uhlmann et al., *Tetrahedron. Lett.* 215, 3539–3542, 1987.

Ribozymes

Ribozymes are RNA molecules with catalytic activity. See, e.g., Cech, *Science* 236, 1532–1539; 1987; Cech, *Ann. Rev. Biochem.* 59, 543–568; 1990, Cech, *Curr. Opin. Struct. Biol.* 2, 605–609; 1992, Couture & Stinchcomb, *Trends Genet.* 12, 510–515, 1996. Ribozymes can be used to inhibit gene function by cleaving an RNA sequence, as is known in the art (e.g., Haseloff et al., U.S. Pat. No. 5,641,673). The mechanism of ribozyme action involves sequence-specific hybridization of the ribozyme molecule to complementary target RNA, followed by endonucleolytic cleavage. Examples include engineered hammerhead motif ribozyme molecules that can specifically and efficiently catalyze endonucleolytic cleavage of specific nucleotide sequences.

The coding sequence of a human prostasin-like enzyme polynucleotide can be used to generate ribozymes which will specifically bind to mRNA transcribed from the human prostasin-like enzyme polynucleotide. Methods of designing and constructing ribozymes which can cleave other RNA molecules in trans in a highly sequence specific manner have been developed and described in the art (see Haseloff et al. *Nature* 334, 585–591, 1988). For example, the cleavage activity of ribozymes can be targeted to specific RNAs by engineering a discrete "hybridization" region into the ribozyme. The hybridization region contains a sequence complementary to the target RNA and thus specifically hybridizes with the target (see, for example, Gerlach et al., EP 321,201).

Specific ribozyme cleavage sites within a human prostasin-like human prostasin-like enzyme RNA target can be identified by scanning the target molecule for ribozyme cleavage sites which include the following sequences: GUA, GUU, and GUC. Once identified, short RNA sequences of between 15 and 20 ribonucleotides corresponding to the region of the target RNA containing the cleavage site can be evaluated for secondary structural features which may render the target inoperable. Suitability of candidate human prostasin-like enzyme RNA targets also can be evaluated by testing accessibility to hybridization with complementary oligonucleotides using ribonuclease protection assays. Longer complementary sequences can be used to increase the affinity of the hybridization sequence for the target. The hybridizing and cleavage regions of the ribozyme can be integrally related such that upon hybridizing to the target RNA through the complementary regions, the catalytic region of the ribozyme can cleave the target.

Ribozymes can be introduced into cells as part of a DNA construct. Mechanical methods, such as microinjection, liposome-mediated transfection, electroporation, or calcium phosphate precipitation, can be used to introduce a ribozyme-containing DNA construct into cells in which it is desired to decrease human prostasin-like enzyme expression. Alternatively, if it is desired that the cells stably retain the DNA construct, the construct can be supplied on a plasmid and maintained as a separate element or integrated into the genome of the cells, as is known in the art. A ribozyme-encoding DNA construct can include transcriptional regulatory elements, such as a promoter element, an enhancer or UAS element, and a transcriptional terminator signal, for controlling transcription of ribozymes in the cells.

As taught in Haseloff et al., U.S. Pat. No. 5,641,673, ribozymes can be engineered so that ribozyme expression will occur in response to factors which induce expression of a target gene. Ribozymes also can be engineered to provide an additional level of regulation, so that destruction of mRNA occurs only when both a ribozyme and a target gene are induced in the cells.

Differentially Expressed Genes

Described herein are methods for the identification of genes whose products interact with human prostasin-like enzyme. Such genes may represent genes that are differentially expressed in disorders including, but not limited to, COPD, CNS disorders, and cancer. Further, such genes may represent genes that are differentially regulated in response to manipulations relevant to the progression or treatment of such diseases. Additionally, such genes may have a temporally modulated expression, increased or decreased at different stages of tissue or organism development. A differentially expressed gene may also have its expression modulated under control versus experimental conditions. In addition, the human prostasin-like enzyme gene or gene product may itself be tested for differential expression.

The degree to which expression differs in a normal versus a diseased state need only be large enough to be visualized via standard characterization techniques such as differential display techniques. Other such standard characterization techniques by which expression differences may be visualized include but are not limited to, quantitative RT (reverse transcriptase), PCR, and Northern analysis.

Identification of Differentially Expressed Genes

To identify differentially expressed genes total RNA or, preferably, mRNA is isolated from tissues of interest. For example, RNA samples are obtained from tissues of experimental subjects and from corresponding tissues of control subjects. Any RNA isolation technique that does not select against the isolation of mRNA may be utilized for the purification of such RNA samples. See, for example, Ausubel et al., ed., CURRENT PROTOCOLS IN MOLECULAR BIOLOGY, John Wiley & Sons, Inc. New York, 1987–1993. Large numbers of tissue samples may readily be processed using techniques well known to those of skill in the art, such as, for example, the single-step RNA isolation process of Chomczynski, U.S. Pat. No. 4,843,155.

Transcripts within the collected RNA samples that represent RNA produced by differentially expressed genes are identified by methods well known to those of skill in the art. They include, for example, differential screening (Tedder et al., Proc. Natl. Acad. Sci. U.S.A. 85, 208–12, 1988), subtractive hybridization (Hedrick et al., Nature 308, 149–53; Lee et al., Proc. Natl. Acad. Sci. U.S.A. 88, 2825, 1984), and differential display (Liang & Pardee, Science 257, 967–71, 1992; U.S. Pat. No. 5,262,311), and microarrays.

The differential expression information may itself suggest relevant methods for the treatment of disorders involving the human prostasin-like enzyme. For example, treatment may include a modulation of expression of the differentially expressed genes and/or the gene encoding the human prostasin-like enzyme. The differential expression information may indicate whether the expression or activity of the differentially expressed gene or gene product or the human prostasin-like enzyme gene or gene product are up-regulated or down-regulated.

Screening Methods

The invention provides assays for screening test compounds which bind to or modulate the activity of a human prostasin-like enzyme polypeptide or a human prostasin-lice enzyme polynucleotide. A test compound preferably binds to a human prostasin-like enzyme polypeptide or polynucleotide. More preferably, a test compound decreases or increases human prostasin-like by at least about 10, preferably about 50, more preferably about 75, 90, or 100% relative to the absence of the test compound.

Test Compounds

Test compounds can be pharmacologic agents already known in the art or can be compounds previously unknown to have any pharmacological activity. The compounds can be naturally occurring or designed in the laboratory. They can be isolated from microorganisms, animals, or plants, and can be produced recombinantly, or synthesized by chemical methods known in the art. If desired, test compounds can be obtained using any of the numerous combinatorial library methods known in the art, including but not limited to, biological libraries, spatially addressable parallel solid phase or solution phase libraries, synthetic library methods requiring deconvolution, the "one-bead one-compound" library method, and synthetic library methods using affinity chromatography selection. The biological library approach is limited to polypeptide libraries, while the other four approaches are applicable to polypeptide, non-peptide oligomer, or small molecule libraries of compounds. See Lam, Anticancer Drug Des. 12, 145, 1997.

Methods for the synthesis of molecular libraries are well known in the art (see, for example, DeWitt et al., Proc. Natl. Acad. Sci. U.S.A. 90, 6909, 1993; Erb et al. Proc. Natl. Acad. Sci. U.S.A. 91, 11422, 1994; Zuckermann et al., J. Med. Chem. 37, 2678, 1994; Cho et al., Science 261, 1303, 1993; Carell et al., Angew. Chem. Int. Ed. Engl. 33, 2059, 1994; Carell et al., Angew. Chem. Int. Ed. Engl. 33, 2061; Gallop et al., J. Med. Chem. 37, 1233, 1994). Libraries of compounds can be presented in solution (see, e.g., Houghten, BioTechniques 13, 412–421, 1992), or on beads (Lam, Nature 354, 82–84, 1991), chips (Fodor, Nature 364, 555–556, 1993), bacteria or spores (Ladner, U.S. Pat. No. 5,223,409), plasmids (Cull et al., Proc. Natl. Acad. Sci. U.S.A. 89, 1865–1869, 1992), or phage (Scott & Smith, Science 249, 386–390, 1990; Devlin, Science 249, 404–406, 1990); Cwirla et al., Proc. Natl. Acad. Sci. 97, 6378–6382, 1990; Felici, J. Mol. Biol. 222, 301–310, 1991; and Ladner, U.S. Pat. No. 5,223,409).

High Throughput Screening

Test compounds can be screened for the ability to bind to human prostasin-like enzyme polypeptides or polynucleotides or to affect human prostasin-like enzyme activity or human prostasin-like enzyme gene expression using high throughput screening. Using high throughput screening, many discrete compounds can be tested in parallel so that large numbers of test compounds can be quickly screened. The most widely established techniques utilize 96-well microtiter plates. The wells of the microtiter plates typically require assay volumes that range from 50 to 500 µl. In addition to the plates, many instruments, materials, pipettors, robotics, plate washers, and plate readers are commercially available to fit the 96-well format.

Alternatively, "free format assays," or assays that have no physical barrier between samples, can be used. For example, an assay using pigment cells (melanocytes) in a simple homogeneous assay for combinatorial peptide libraries is described by Jayawickreme et al., Proc. Natl. Acad. Sci. U.S.A. 19, 1614–18 (1994). The cells are placed under agarose in petri dishes, then beads that carry combinatorial compounds are placed on the surface of the agarose. The combinatorial compounds are partially released the compounds from the beads. Active compounds can be visualized as dark pigment areas because, as the compounds diffuse locally into the gel matrix, the active compounds cause the cells to change colors.

Another example of a free format assay is described by Chelsky, "Strategies for Screening Combinatorial Libraries: Novel and Traditional Approaches," reported at the First Annual Conference of The Society for Biomolecular Screening in Philadelphia, Pa. (Nov. 7–10, 1995). Chelsky placed a simple homogenous enzyme assay for carbonic anhydrase inside an agarose gel such that the enzyme in the gel would cause a color change throughout the gel. Thereafter, beads carrying combinatorial compounds via a photolinker were placed inside the gel and the compounds were partially released by UV-light. Compounds that inhibited the enzyme were observed as local zones of inhibition having less color change.

Yet another example is described by Salmon et al., *Molecular Diversity* 2, 57–63 (1996). In this example, combinatorial libraries were screened for compounds that had cytotoxic effects on cancer cells growing in agar.

Another high throughput screening method is described in Beutel et al., U.S. Pat. No. 5,976,813. In this method, test samples are placed in a porous matrix. One or more assay components are then placed within, on top of, or at the bottom of a matrix such as a gel, a plastic sheet, a filter, or other form of easily manipulated solid support. When samples are introduced to the porous matrix they diffuse sufficiently slowly, such that the assays can be performed without the test samples running together.

Binding Assays

For binding assays, the test compound is preferably a small molecule which binds to and occupies, for example, the ATP/GTP binding site of the enzyme or the active site of the human prostasin-like enzyme polypeptide, such that normal biological activity is prevented. Examples of such small molecules include, but are not limited to, small peptides or peptide-like molecules.

In binding assays, either the test compound or the human prostasin-like enzyme polypeptide can comprise a detectable label, such as a fluorescent, radioisotopic, chemiluminescent, or enzymatic label, such as horseradish peroxidase, alkaline phosphatase, or luciferase. Detection of a test compound which is bound to the human prostasin-like enzyme polypeptide can then be accomplished, for example, by direct counting of radioemmission, by scintillation counting, or by determining conversion of an appropriate substrate to a detectable product.

Alternatively, binding of a test compound to a human prostasin-like enzyme polypeptide can be determined without labeling either of the interactants. For example, a microphysiometer can be used to detect binding of a test compound with a human prostasin-like enzyme polypeptide. A microphysiometer (e.g., Cytosensor™) is an analytical instrument that measures the rate at which a cell acidifies its environment using a light-addressable potentiometric sensor (LAPS). Changes in this acidification rate can be used as an indicator of the interaction between a test compound and a human prostasin-like enzyme polypeptide (McConnell et al., *Science* 257, 1906–1912, 1992).

Determining the ability of a test compound to bind to a human prostasin-like enzyme polypeptide also can be accomplished using a technology such as real-time Bimolecular Interaction Analysis (BIA) (Sjolander & Urbaniczky, *Anal. Chem.* 63, 2338–2345, 1991, and Szabo et al., *Curr. Opin. Struct. Biol.* 5, 699–705, 1995). BIA is a technology for studying biospecific interactions in real time, without labeling any of the interactants (e.g., BIAcore™). Changes in the optical phenomenon surface plasmon resonance (SPR) can be used as an indication of real-time reactions between biological molecules.

In yet another aspect of the invention, a human prostasin-like enzyme polypeptide can be used as a "bait protein" in a two-hybrid assay or three-hybrid assay (see, e.g., U.S. Pat. No. 5,283,317; Zervos et al., *Cell* 72, 223–232, 1993; Madura et al., *J. Biol. Chem.* 268, 12046–12054, 1993; Bartel et al., *BioTechniques* 14, 920–924, 1993; Iwabuchi et al., *Oncogene* 8, 1693–1696, 1993; and Brent WO94/10300), to identify other proteins which bind to or interact with the human prostasin-like enzyme polypeptide and modulate its activity.

The two-hybrid system is based on the modular nature of most transcription factors, which consist of separable DNA-binding and activation domains. Briefly, the assay utilizes two different DNA constructs. For example, in one construct, polynucleotide encoding a human prostasin-like enzyme polypeptide can be fused to a polynucleotide encoding the DNA binding domain of a known transcription factor (e.g., GAL-4). In the other construct a DNA sequence that encodes an unidentified protein ("prey" or "sample") can be fused to a polynucleotide that codes for the activation domain of the known transcription factor. If the "bait" and the "prey" proteins are able to interact in vivo to form an protein-dependent complex, the DNA-binding and activation domains of the transcription factor are brought into close proximity. This proximity allows transcription of a reporter gene (e.g., LacZ), which is operably linked to a transcriptional regulatory site responsive to the transcription factor. Expression of the reporter gene can be detected, and cell colonies containing the functional transcription factor can be isolated and used to obtain the DNA sequence encoding the protein which interacts with the human prostasin-like enzyme polypeptide.

It may be desirable to immobilize either the human prostasin-like enzyme polypeptide (or polynucleotide) or the test compound to facilitate separation of bound from unbound forms of one or both of the interactants, as well as to accommodate automation of the assay. Thus, either the human prostasin-like enzyme polypeptide (or polynucleotide) or the test compound can be bound to a solid support. Suitable solid supports include, but are not limited to, glass or plastic slides, tissue culture plates, microtiter wells, tubes, silicon chips, or particles such as beads (including, but not limited to, latex, polystyrene, or glass beads). Any method known in the art can be used to attach the human prostasin-like enzyme polypeptide (or polynucleotide) or test compound to a solid support, including use of covalent and non-covalent linkages, passive absorption, or pairs of binding moieties attached respectively to the polypeptide (or polynucleotide) or test compound and the solid support. Test compounds are preferably bound to the solid support in an array, so that the location of individual test compounds can be tracked. Binding of a test compound to a human prostasin-like enzyme polypeptide (or polynucleotide) can be accomplished in any vessel suitable for containing the reactants. Examples of such vessels include microtiter plates, test tubes, and microcentrifuge tubes.

In one embodiment, the human prostasin-like enzyme polypeptide is a fusion protein comprising a domain that allows the human prostasin-like enzyme polypeptide to be bound to a solid support. For example, glutathione-S-transferase fusion proteins can be adsorbed onto glutathione sepharose beads (Sigma Chemical, St. Louis, Mo.) or glutathione derivatized microtiter plates, which are then combined with the test compound or the test compound and the non-adsorbed human prostasin-like enzyme polypeptide; the mixture is then incubated under conditions conducive to complex formation (e.g., at physiological conditions for salt and pH). Following incubation, the beads or microtiter plate wells are washed to remove any unbound components. Binding of the interactants can be determined either directly or indirectly, as described above. Alternatively, the complexes can be dissociated from the solid support before binding is determined.

Other techniques for immobilizing proteins or polynucleotides on a solid support also can be used in the screening assays of the invention. For example, either a human prostasin-like enzyme polypeptide (or polynucleotide) or a test compound can be immobilized utilizing conjugation of biotin and streptavidin. Biotinylated human prostasin-like enzyme polypeptides (or polynucleotides) or test compounds can be prepared from biotin-NHS(N-hydroxysuccinimide) using techniques well known in the art (e.g., biotinylation kit, Pierce Chemicals, Rockford, Ill.) and immobilized in the wells of streptavidin-coated 96 well plates (Pierce Chemical). Alternatively, antibodies which specifically bind to a human prostasin-like enzyme polypeptide, polynucleotide, or a test compound, but which do not interfere with a desired binding site, such as the ATP/GTP binding site or the active site of the human prostasin-like enzyme polypeptide, can be derivatized to the wells of the plate. Unbound target or protein can be trapped in the wells by antibody conjugation.

Methods for detecting such complexes, in addition to those described above for the GST-immobilized complexes, include immunodetection of complexes using antibodies which specifically bind to the human prostasin-like enzyme polypeptide or test compound, enzyme-linked assays which rely on detecting an activity of the human prostasin-like enzyme polypeptide, and SDS gel electrophoresis under non-reducing conditions.

Screening for test compounds which bind to a human prostasin-like enzyme polypeptide or polynucleotide also can be carried out in an intact cell. Any cell which comprises a human prostasin-like enzyme polypeptide or polynucleotide can be used in a cell-based assay system. A human prostasin-like enzyme polynucleotide can be naturally occurring in the cell or can be introduced using techniques such as those described above. Binding of the test compound to a human prostasin-like enzyme polypeptide or polynucleotide is determined as described above.

Enzyme Assays

Test compounds can be tested for the ability to increase or decrease the human prostasin-like activity of a human prostasin-like enzyme polypeptide. Human prostasin-like enzyme activity can be measured, for example, as described in Yu et al., *J. Biol. Chem.* 269, 18843–48, 1994.

Enzyme assays can be carried out after contacting either a purified human prostasin-like enzyme polypeptide, a cell membrane preparation, or an intact cell with a test compound. A test compound which decreases a serine protease activity of a human prostasin-like enzyme polypeptide by at least about 10, preferably about 50, more preferably about 75, 90, or 100% is identified as a potential therapeutic agent for decreasing human prostasin-like enzyme activity. A test compound which increases a serine protease activity of a human prostasin-like enzyme polypeptide by at least about 10, preferably about 50, more preferably about 75, 90, or 100% is identified as a potential therapeutic agent for increasing human prostasin-like enzyme activity.

Gene Expression

In another embodiment, test compounds which increase or decrease human prostasin-like enzyme gene expression are identified. A human prostasin-like enzyme polynucleotide is contacted with a test compound, and the expression of an RNA or polypeptide product of the human prostasin-like enzyme polynucleotide is determined. The level of expression of appropriate mRNA or polypeptide in the presence of the test compound is compared to the level of expression of mRNA or polypeptide in the absence of the test compound. The test compound can then be identified as a modulator of expression based on this comparison. For example, when expression of mRNA or polypeptide is greater in the presence of the test compound than in its absence, the test compound is identified as a stimulator or enhancer of the mRNA or polypeptide expression. Alternatively, when expression of the mRNA or polypeptide is less in the presence of the test compound than in its absence, the test compound is identified as an inhibitor of the mRNA or polypeptide expression.

The level of human prostasin-like enzyme mRNA or polypeptide expression in the cells can be determined by methods well known in the art for detecting mRNA or polypeptide. Either qualitative or quantitative methods can be used. The presence of polypeptide products of a human prostasin-like enzyme polynucleotide can be determined, for example, using a variety of techniques known in the art, including immunochemical methods such as radioimmunoassay, Western blotting, and immunohistochemistry. Alternatively, polypeptide synthesis can be determined in vivo, in a cell culture, or in an in vitro translation system by detecting incorporation of labeled amino acids into a human prostasin-like enzyme polypeptide.

Such screening can be carried out either in a cell-free assay system or in an intact cell. Any cell which expresses a human prostasin-like enzyme polynucleotide can be used in a cell-based assay system. The human prostasin-like enzyme polynucleotide can be naturally occurring in the cell or can be introduced using techniques such as those described above. Either a primary culture or an established cell line, such as CHO or human embryonic kidney 293 cells, can be used.

Pharmaceutical Compositions

The invention also provides pharmaceutical compositions which can be administered to a patient to achieve a therapeutic effect. Pharmaceutical compositions of the invention can comprise a prostasin-like enzyme polypeptide, prostasin-like enzyme polynucleotide, antibodies which specifically bind to a prostasin-like enzyme polypeptide, or mimetics, agonists, antagonists, or inhibitors of a prostasin-like enzyme polypeptide. The compositions can be administered alone or in combination with at least one other agent, such as stabilizing compound, which can be administered in any sterile, biocompatible pharmaceutical carrier, including, but not limited to, saline, buffered saline, dextrose, and water. The compositions can be administered to a patient alone, or in combination with other agents, drugs or hormones.

In addition to the active ingredients, these pharmaceutical compositions can contain suitable pharmaceutically-acceptable carriers comprising excipients and auxiliaries which facilitate processing of the active compounds into preparations which can be used pharmaceutically. Pharmaceutical compositions of the invention can be administered by any number of routes including, but not limited to, oral, intravenous, intramuscular, intra-arterial, intramedullary, intrathecal, intraventricular, transdermal, subcutaneous, intraperitoneal, intranasal, parenteral, topical, sublingual, or rectal means. Pharmaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions, and the like, for ingestion by the patient.

Pharmaceutical preparations for oral use can be obtained through combination of active compounds with solid excipient, optionally grinding a resulting mixture, and processing the mixture of granules, after adding suitable auxiliaries, if desired, to obtain tablets or dragee cores. Suitable excipients are carbohydrate or protein fillers, such as sugars, including lactose, sucrose, mannitol, or sorbitol; starch from corn, wheat, rice, potato, or other plants; cellulose, such as methyl cellulose, hydroxypropylmethyl-cellulose, or sodium carboxymethylcellulose; gums including arabic and tragacanth; and proteins such as gelatin and collagen. If desired, disintegrating or solubilizing agents can be added, such as the cross-linked polyvinyl pyrrolidone, agar, alginic acid, or a salt thereof, such as sodium alginate.

Dragee cores can be used in conjunction with suitable coatings, such as concentrated sugar solutions, which also can contain gum arabic, talc, polyvinylpyrrolidone, carbopol gel, polyethylene glycol, and/or titanium dioxide, lacquer solutions, and suitable organic solvents or solvent mixtures. Dyestuffs or pigments can be added to the tablets or dragee coatings for product identification or to characterize the quantity of active compound, i.e., dosage.

Pharmaceutical preparations which can be used orally include push-fit capsules made of gelatin, as well as soft, sealed capsules made of gelatin and a coating, such as glycerol or sorbitol. Push-fit capsules can contain active ingredients mixed with a filler or binders, such as lactose or starches, lubricants, such as talc or magnesium stearate, and, optionally, stabilizers. In soft capsules, the active compounds can be dissolved or suspended in suitable liquids, such as fatty oils, liquid, or liquid polyethylene glycol with or without stabilizers.

Pharmaceutical formulations suitable for parenteral administration can be formulated in aqueous solutions, preferably in physiologically compatible buffers such as Hanks' solution, Ringer's solution, or physiologically buffered saline. Aqueous injection suspensions can contain substances which increase the viscosity of the suspension, such as sodium carboxymethyl cellulose, sorbitol, or dextran. Additionally, suspensions of the active compounds can be prepared as appropriate oily injection suspensions. Suitable lipophilic solvents or vehicles include fatty oils such as sesame oil, or synthetic fatty acid esters, such as ethyl oleate or triglycerides, or liposomes. Non-lipid polycationic amino polymers also can be used for delivery. Optionally, the suspension also can contain suitable stabilizers or agents which increase the solubility of the compounds to allow for the preparation of highly concentrated solutions. For topical or nasal administration, penetrants appropriate to the particular barrier to be permeated are used in the formulation. Such penetrants are generally known in the art.

The pharmaceutical compositions of the present invention can be manufactured in a manner that is known in the art, e.g., by means of conventional mixing, dissolving, granulating, dragee-making, levigating, emulsifying, encapsulating, entrapping, or lyophilizing processes. The pharmaceutical composition can be provided as a salt and can be formed with many acids, including but not limited to, hydrochloric, sulfuric, acetic, lactic, tartaric, malic, succinic, etc. Salts tend to be more soluble in aqueous or other protonic solvents than are the corresponding free base forms. In other cases, the preferred preparation can be a lyophilized powder which can contain any or all of the following: 1–50 mM histidine, 0.1%–2% sucrose, and 2–7% mannitol, at a pH range of 4.5 to 5.5, that is combined with buffer prior to use.

Further details on techniques for formulation and administration can be found in the latest edition of REMINGTON'S PHARMACEUTICAL SCIENCES (Maack Publishing Co., Easton, Pa.). After pharmaceutical compositions have been prepared, they can be placed in an appropriate container and labeled for treatment of an indicated condition. Such labeling would include amount, frequency, and method of administration.

Therapeutic Indications and Methods

1. Tumor Cell Invasion and Metastasis. The human prostasin-like enzyme gene provides a therapeutic target for decreasing human prostasin-like enzyme activity, in particular for treating or preventing metastatic cancer. Cancer is a disease fundamentally caused by oncogenic cellular transformation. There are several hallmarks of transformed cells that distinguish them from their normal counterparts and underlie the pathophysiology of cancer. These include uncontrolled cellular proliferation, unresponsiveness to normal death-inducing signals (immortalization), increased cellular motility and invasiveness, increased ability to recruit blood supply through induction of new blood vessel formation (angiogenesis), genetic instability, and dysregulated gene expression. Various combinations of these aberrant physiologies, along with the acquisition of drug-resistance frequently lead to an intractable disease state in which organ failure and patient death ultimately ensue.

Most standard cancer therapies target cellular proliferation and rely on the differential proliferative capacities between transformed and normal cells for their efficacy. This approach is hindered by the facts that several important normal cell types are also highly proliferative and that cancer cells frequently become resistant to these agents. Thus, the therapeutic indices for traditional anti-cancer therapies rarely exceed 2.0.

The advent of genomics-driven molecular target identification has opened up the possibility of identifying new cancer-specific targets for therapeutic intervention that will provide safer, more effective treatments for cancer patients. Thus, newly discovered tumor-associated genes and their products can be tested for their role(s) in disease and used as tools to discover and develop innovative therapies. Genes playing important roles in any of the physiological processes outlined above can be characterized as cancer targets.

Genes or gene fragments identified through genomics can readily be expressed in one or more heterologous expression systems to produce functional recombinant proteins. These proteins are characterized in vitro for their biochemical properties and then used as tools in high-throughput molecular screening programs to identify chemical modulators of their biochemical activities. Agonists and/or antagonists of target protein activity can be identified in this manner and subsequently tested in cellular and in vivo disease models for anti-cancer activity. Optimization of lead compounds with iterative testing in biological models and detailed pharmacokinetic and toxicological analyses form the basis for drug development and subsequent testing in humans.

For example, blocking a fibronectin domain of human prostasin-like enzyme can suppress or prevent migration or metastasis of tumor cells in response to fibronectin (9, 10). Cancers whose metastasis can be suppressed according to the invention include adenocarcinoma, melanoma, cancers of the adrenal gland, bladder, bone, breast, cervix, gall bladder, liver, lung, ovary, pancreas, prostate, testis, and uterus. Circulating tumor cells arrested in the capillary beds of different organs must invade the endothelial cell lining and degrade its underlying basement membrane (BM) in order to invade into the extravascular tissue(s) where they establish metastasis (1, 2). Metastatic tumor cells often attach at or near the intercellular junctions between adjacent endothelial cells. Such attachment of the metastatic cells is followed by rupture of the junctions, retraction of the endothelial cell borders and migration through the breach in the endothelium toward the exposed underlying BM (1, 11).

Once located between endothelial cells and the BM, the invading cells must degrade the subendothelial glycoproteins and proteoglycans of the BM in order to migrate out of the vascular compartment. Several cellular enzymes (e.g., collagenase IV, plasminogen activator, cathepsin B, elastase) are thought to be involved in degradation of BM (2, 11). Suppression of human prostasin-like enzyme activity therefore can be used to suppress tumor cell invasion and metastasis.

2. Tumor Angiogenesis. Basic fibroblast growth factor (bFGF) has been extracted from the subendothelial extracellular matrix produced in vitro (3) and from basement membranes of the cornea (4), suggesting that extracellular matrix may serve as a reservoir for bFGF. Immunohistochemical staining revealed the localization of bFGF in basement membranes of diverse tissues and blood vessels (5). Despite the ubiquitous presence of bFGF in normal tissues, endothelial cell proliferation in these tissues is usually very low, which suggests that bFGF is somehow sequestered from its site of action. It is possible, therefore, that suppression of human prostasin-like enzyme activity can suppress release of active bFGF from extracellular matrix and basement membranes. In addition, displacement of bFGF from its storage within basement membranes and extracellular matrix may therefore provide a novel mechanism for induction of neovascularization in normal and pathological situations. Restriction of endothelial cell growth factors in the extracellular matrix may prevent their systemic action on the vascular endothelium, thus maintaining a very low rate of endothelial cells turnover and vessel growth. On the other hand, release of bFGF from storage in the extracellular matrix may elicit localized endothelial cell proliferation and neovascularization in processes such as wound healing, inflammation and tumor development (6, 7).

3. Inflammation and Cellular Immunity. Prostasin-like enzyme activity may be involved in the ability of activated cells of the immune system to leave the circulation and elicit both inflammatory and autoimmune responses. Thus, inflammation and cellular immunity may be regulated by regulating activity of prostasin-like enzyme.

4. Viral infection. Removal of the cell surface components by prostasin-like enzyme may influence the ability of viruses to attach to the cell surface. Regulation of prostasin-like enzyme may therefore be used to treat viral infections.

5. Neurodegenerative diseases. It is also possible that prostasin-like enzyme activity can be used to degrade, for example, prion protein amyloid plaques of Genstmann-Straussler Syndrome, Creutzfeldt-Jakob disease, and Scrapie.

6. Restenosis and Atherosclerosis. Proliferation of arterial smooth muscle cells (SMCs) in response to endothelial injury and accumulation of cholesterol rich lipoproteins are basic events in the pathogenesis of atherosclerosis and restenosis (8). It is possible that prostasin-like enzyme may be involved in the catabolic pathway that may allow substantial cellular and interstitial accumulation of cholesterol rich lipoproteins. The latter pathway is expected to be highly atherogenic by promoting accumulation of apoB and apoE rich lipoproteins (i.e. LDL, VLDL, chylomicrons), independent of feedback inhibition by the cellular sterol content. Altered levels of human prostasin-like enzyme activity therefore may inhibit both SMC proliferation and lipid accumulation and thus may halt the progression of restenosis and atherosclerosis.

7. Osteoporosis. Osteoporosis is a disease characterized by low bone mass and microarchitectural deterioration of bone tissue, leading to enhanced bone fragility and a consequent increase in fracture risk. It is the most common human metabolic bone disorder. Established osteoporosis includes the presence of fractures.

Bone turnover occurs by the action of two major effector cell types within bone: the osteoclast, which is responsible for bone resorption, and the osteoblast, which synthesizes and mineralizes bone matrix. The actions of osteoclasts and osteoblasts are highly coordinated. Osteoclast precursors are recruited to the site of turnover; they differentiate and fuse to form mature osteoclasts which then resorb bone. Attached to the bone surface, osteoclasts produce an acidic microenvironment in a tightly defined junction between the specialized osteoclast border membrane and the bone matrix, thus allowing the localized solubilization of bone matrix. This in turn facilitates the proteolysis of demineralized bone collagen. Matrix degradation is thought to release matrix-associated growth factor and cytokines, which recruit osteoblasts in a temporally and spatially controlled fashion. Osteoblasts synthesize and secrete new bone matrix proteins, and subsequently mineralize this new matrix. In the normal skeleton this is a physiological process which does not result in a net change in bone mass. In pathological states, such as osteoporosis, the balance between resorption and formation is altered such that bone loss occurs. See WO 99/45923.

The osteoclast itself is the direct or indirect target of all currently available osteoporosis agents with the possible exception of fluoride. Antiresorptive therapy prevents further bone loss in treated individuals. Osteoblasts are derived from multipotent stem cells which reside in bone marrow and also gives rise to adipocytes, chondrocytes, fibroblasts and muscle cells. Selective enhancement of osteoblast activity is a highly desirable goal for osteoporosis therapy since it would result in an increase in bone mass, rather than a prevention of further bone loss. An effective anabolic therapy would be expected to lead to a significantly greater reduction in fracture risk than currently available treatments.

The agonists or antagonists to the newly discovered polypeptides may act as antiresorptive by directly altering the osteoclast differentiation, osteoclast adhesion to the bone matrix or osteoclast function of degrading the bone matrix. The agonists or antagonists could indirectly alter the osteoclast function by interfering in the synthesis and/or modification of effector molecules of osteoclast differentiation or function such as cytokines, peptide or steroid hormones, proteases, etc.

The agonists or antagonists to the newly discovered polypeptides may act as anabolics by directly enhancing the osteoblast differentiation and/or its bone matrix forming function. The agonists or antagonists could also indirectly alter the osteoblast function by enhancing the synthesis of growth factors, peptide or steroid hormones or decreasing the synthesis of inhibitory molecules.

The agonists and antagonists may be used to mimic, augment or inhibit the action of the newly discovered polypeptides which may be useful to treat osteoporosis, Paget's disease, degradation of bone implants particularly dental implants.

8. COPD. Chronic obstructive pulmonary (or airways) disease (COPD) is a condition defined physiologically as airflow obstruction that generally results from a mixture of emphysema and peripheral airway obstruction due to chronic bronchitis (Senior & Shapiro, *Pulmonary Diseases and Disorders,* 3d ed., New York, McGraw-Hill, 1998, pp. 659–681, 1998; Barnes, *Chest* 117, 10S–14S, 2000). Emphysema is characterized by destruction of alveolar walls leading to abnormal enlargement of the air spaces of the lung. Chronic bronchitis is defined clinically as the presence of chronic productive cough for three months in each of two successive years. In COPD, airflow obstruction is usually progressive and is only partially reversible. By far the most important risk factor for development of COPD is cigarette smoking, although the disease does occur in non-smokers.

Chronic inflammation of the airways is a key pathological feature of COPD (Senior & Shapiro, 1998). The inflammatory cell population comprises increased numbers of macrophages, neutrophils, and CD8+ lymphocytes. Inhaled irritants, such as cigarette smoke, activate macrophages which are resident in the respiratory tract, as well as epithelial cells leading to release of chemokines (e.g., interleukin-8) and other chemotactic factors. These chemotactic factors act to increase the neutrophil/monocyte trafficking from the blood into the lung tissue and airways. Neutrophils and monocytes recruited into the airways can release a variety of potentially damaging mediators such as proteolytic enzymes and reactive oxygen species. Matrix degradation and emphysema, along with airway wall thickening, surfactant dysfunction, and mucus hypersecretion, all are potential sequelae of this inflammatory response that lead to impaired airflow and gas exchange.

COPD is characterized by damage to the lung extracellular matrix and emphysema can be viewed as the pathologic process that affects the lung parenchyma. This process eventually leads to the destruction of the airway walls resulting in permanent airspace enlargement (Senior and Shapiro, in PULMONARY DISEASES AND DISORDERS, 3$^{rd}$ ed., New York, McGraw-Hill, 1998, pp. 659–681, 1998). The observation that inherited deficiency of al-antitrypsin (al-AT), the primary inhibitor of neutrophil elastase, predisposes individuals to early onset emphysema, and that intrapulmonary instillation of elastolytic enzymes in experimental animals causes emphysema, led to the elastase:antielastase hypothesis for the pathogenesis of emphysema (Eriksson, *Acta Med. Scand.* 177(*Suppl.*), 432, 1965, Gross, *J. Occup. Med.* 6, 481–84, 1964). This in turn led to the concept that destruction of elastin in the lung parenchyma is the basis of the development of emphysema.

A broad range of immune and inflammatory cells including neutrophils, macrophages, T lymphocytes and eosinophils contain proteolytic enzymes that could contribute to the destruction of lung extracellular matrix (Shapiro, 1999). In addition, a number of different classes of proteases have been identified that have the potential to contribute to lung matrix destruction. These include serine proteases, matrix metalloproteinases and cysteine proteases. Of these classes of enzymes, a number can hydrolyze elastin and have been shown to be elevated in COPD patients (neutrophil elastase, MMP-2, 9, 12) (Culpitt et al., *Am. J. Respir. Crit. Care Med.* 160, 1635–39, 1999, Shapiro, *Am. J. Crit. Care Med.* 160 (5), S29–S32,1999).

It is expected that in the future novel members of the existing classes of proteases and new classes of proteases will be identified that play a significant role in the damage of the extracellular lung matrix including elastin proteolysis. Novel protease targets therefore remain very attractive therapeutic targets.

9. Other therapeutic and diagnostic indications. Anti-human prostasin-like enzyme antibodies can be applied for immunodetection and diagnosis of micrometastases, autoimmune lesions, and renal failure in biopsy specimens, plasma samples, and body fluids. Alternatively, if desired a prostasin-like enzyme function can be supplied to a cell by introducing a prostasin-like enzyme-encoding polynucleotide into the cell.

The invention further pertains to the use of novel agents identified by the screening assays described above. Accordingly, it is within the scope of this invention to use a test compound identified as described herein in an appropriate animal model. For example, an agent identified as described herein (e.g., a modulating agent, an antisense nucleic acid molecule, a specific antibody, ribozyme, or a polypeptide-binding partner) can be used in an animal model to determine the efficacy, toxicity, or side effects of treatment with such an agent. Alternatively, an agent identified as described herein can be used in an animal model to determine the mechanism of action of such an agent. Furthermore, this invention pertains to uses of novel agents identified by the above-described screening assays for treatments as described herein.

A reagent which affects prostasin-like enzyme activity can be administered to a human cell, either in vitro or in vivo, to reduce prostasin-like enzyme activity. The reagent preferably binds to an expression product of a human prostasin-like enzyme gene. If the expression product is a polypeptide, the reagent is preferably an antibody. For treatment of human cells ex vivo, an antibody can be added to a preparation of stem cells which have been removed from the body. The cells can then be replaced in the same or another human body, with or without clonal propagation, as is known in the art.

In one embodiment, the reagent is delivered using a liposome. Preferably, the liposome is stable in the animal into which it has been administered for at least about 30 minutes, more preferably for at least about 1 hour, and even more preferably for at least about 24 hours. A liposome comprises a lipid composition that is capable of targeting a reagent, particularly a polynucleotide, to a particular site in an animal, such as a human. Preferably, the lipid composition of the liposome is capable of targeting to a specific organ of an animal, such as the lung or liver.

A liposome useful in the present invention comprises a lipid composition that is capable of fusing with the plasma membrane of the targeted cell to deliver its contents to the cell. Preferably, the transfection efficiency of a liposome is about 0.5 µg of DNA per 16 nmole of liposome delivered to about $10^6$ cells, more preferably about 1.0 µg of DNA per 16 nmol of liposome delivered to about $10^6$ cells, and even more preferably about 2.0 µg of DNA per 16 nmol of liposome delivered to about $10^6$ cells. Preferably, a liposome is between about 100 and 500 µm, more preferably between about 150 and 450 nm, and even more preferably between about 200 and 400 nm in diameter.

Suitable liposomes for use in the present invention include those liposomes standardly used in, for example, gene delivery methods known to those of skill in the art.

More preferred liposomes include liposomes having a polycationic lipid composition and/or liposomes having a cholesterol backbone conjugated to polyethylene glycol. Optionally, a liposome comprises a compound capable of targeting the liposome to a tumor cell, such as a tumor cell ligand exposed on the outer surface of the liposome.

Complexing a liposome with a reagent such as an antisense oligonucleotide or ribozyme can be achieved using methods which are standard in the art (see, for example, U.S. Pat. No. 5,705,151). Preferably, from about 0.1 µg to about 10 µg of polynucleotide is combined with about 8 nmol of liposomes, more preferably from about 0.5 µg to about 5 µg of polynucleotides are combined with about 8 nmol liposomes, and even more preferably about 1.0 µg of polynucleotides is combined with about 8 nmol liposomes.

In another embodiment, antibodies can be delivered to specific tissues in vivo using receptor-mediated targeted delivery. Receptor-mediated DNA delivery techniques are taught in, for example, Findeis et al. *Trends in Biotechnol.* 11, 202–05 (1993); Chiou et al., GENE THERAPEUTICS: METHODS AND APPLICATIONS OF DIRECT GENE TRANSFER (J. A. Wolff, ed.) (1994); Wu & Wu, *J. Biol. Chem.* 263, 621–24 (1988); Wu et al., *J. Biol. Chem.* 269, 542–46 (1994); Zenke et al., *Proc. Natl. Acad. Sci. U.S.A.* 87, 3655–59 (1990); Wu et al., *J. Biol. Chem.* 266, 338–42 (1991).

If the reagent is a single-chain antibody, polynucleotides encoding the antibody can be constructed and introduced into a cell either ex vivo or in vivo using well-established techniques including, but not limited to, transferrin-polycation-mediated DNA transfer, transfection with naked or encapsulated nucleic acids, liposome-mediated cellular fusion, intracellular transportation of DNA-coated latex beads, protoplast fusion, viral infection, electroporation, "gene gun," and DEAE- or calcium phosphate-mediated transfection.

Determination of a Therapeutically Effective Dose

The determination of a therapeutically effective dose is well within the capability of those skilled in the art. A therapeutically effective dose refers to that amount of active ingredient which increases or decreases human prostasin-like enzyme activity relative to that which occurs in the absence of the therapeutically effective dose.

For any compound, the therapeutically effective dose can be estimated initially either in cell culture assays or in animal models, usually mice, rabbits, dogs, or pigs. The animal model also can be used to determine the appropriate concentration range and route of administration. Such information can then be used to determine useful doses and routes for administration in humans.

Therapeutic efficacy and toxicity, e.g., $ED_{50}$ (the dose therapeutically effective in 50% of the population) and $LD_{50}$ (the dose lethal to 50% of the population), can be determined by standard pharmaceutical procedures in cell cultures or experimental animals. The dose ratio of toxic to therapeutic effects is the therapeutic index, and it can be expressed as the ratio, $LD_{50}/ED_{50}$.

Pharmaceutical compositions which exhibit large therapeutic indices are preferred. The data obtained from cell culture assays and animal studies is used in formulating a range of dosage for human use. The dosage contained in such compositions is preferably within a range of circulating concentrations that include the $ED_{50}$ with little or no toxicity. The dosage varies within this range depending upon the dosage form employed, sensitivity of the patient, and the route of administration.

The exact dosage will be determined by the practitioner, in light of factors related to the subject that requires treatment. Dosage and administration are adjusted to provide sufficient levels of the active ingredient or to maintain the desired effect. Factors which can be taken into account include the severity of the disease state, general health of the subject, age, weight, and gender of the subject, diet, time and frequency of administration, drug combination(s), reaction sensitivities, and tolerance/response to therapy. Long-acting pharmaceutical compositions can be administered every 3 to 4 days, every week, or once every two weeks depending on the half-life and clearance rate of the particular formulation.

Normal dosage amounts can vary from 0.1 to 100,000 micrograms, up to a total dose of about 1 g, depending upon the route of administration. Guidance as to particular dosages and methods of delivery is provided in the literature and generally available to practitioners in the art. Those skilled in the art will employ different formulations for nucleotides than for proteins or their inhibitors. Similarly, delivery of polynucleotides or polypeptides will be specific to particular cells, conditions, locations, etc.

Effective in vivo dosages of an antibody are in the range of about 5 µg to about 50 µg/kg, about 50 µg to about 5 mg/kg, about 100 µg to about 500 µg/kg of patient body weight, and about 200 to about 250 µg/kg of patient body weight. For administration of polynucleotides encoding single-chain antibodies, effective in vivo dosages are in the range of about 100 ng to about 200 ng, 500 ng to about 50 mg, about 1 µg to about 2 mg, about 5 µg to about 500 µg, and about 20 µg to about 100 µg of DNA.

If the expression product is mRNA, the reagent is preferably an antisense oligonucleotide or a ribozyme. Polynucleotides which express antisense oligonucleotides or ribozymes can be introduced into cells by a variety of methods, as described above.

Preferably, a reagent reduces expression of a prostasin-like enzyme polynucleotide or activity of a prostasin-like enzyme polypeptide by at least about 10, preferably about 50, more preferably about 75, 90, or 100% relative to the absence of the reagent. The effectiveness of the mechanism chosen to decrease the level of expression of a prostasin-like enzyme polynucleotide or the activity of a prostasin-like enzyme polypeptide can be assessed using methods well known in the art, such as hybridization of nucleotide probes to prostasin-like enzyme-specific mRNA, quantitative RT-PCR, immunologic detection of a prostasin-like enzyme polypeptide, or measurement of prostasin-like enzyme activity.

In any of the embodiments described above, any of the pharmaceutical compositions of the invention can be administered in combination with other appropriate therapeutic agents. Selection of the appropriate agents for use in combination therapy can be made by one of ordinary skill in the art, according to conventional pharmaceutical principles. The combination of therapeutic agents can act synergistically to effect the treatment or prevention of the various disorders described above. Using this approach, one may be able to achieve therapeutic efficacy with lower dosages of each agent, thus reducing the potential for adverse side effects.

Any of the therapeutic methods described above can be applied to any subject in need of such therapy, including, for example, mammals such as dogs, cats, cows, horses, rabbits, monkeys, and most preferably, humans.

The above disclosure generally describes the present invention, and all patents, patent applications, and references cited in this disclosure are expressly incorporated herein by reference in their entireties. A more complete understanding can be obtained by reference to the following specific examples, which are provided for purposes of illustration only and are not intended to limit the scope of the invention.

EXAMPLE 1

Detection of Prostasin-like Enzyme Activity

The polynucleotide of SEQ ID NO: 1 or SEQ ID NO: 5 is inserted into the expression vector pCEV4 and the expression vector pCEV4-prostasin-like enzyme polypeptide obtained is transfected into human embryonic kidney 293 cells. From these cells extracts are obtained and protease activity is measured using thiobenzylester substrates, as described in U.S. Pat. No. 5,500,344. For monitoring enzyme activities from granules and column fractions, assays are performed at room temperature using 0.5 mM 5,5'-dithiobis-(2-nitrobenzoic acid) (DTNB) (Sigma) to detect the HSBzl leaving group ($\epsilon_{410}$=13600 M$^{-1}$ cm$^{-1}$).

BLT-esterase activity is estimated using a microtiter assay (Green and Shaw, *Anal. Biochem.* 93, 223–226, 1979). Briefly, 50 µl of sample is added to 100 µl of 1 mM DTNB, made up in 10 mM HEPES, 1 mM CaCl$_2$, 1 mM MgCl$_2$, pH 7.2. The reaction is initiated by the addition of 50 µl of BLT (Sigma) to give a final concentration of 500 µM. For Metase determinations, 50 µl of dilutions of the sample in 0.1 M HEPES, 0.05 M CaCl$_2$, pH 7.5, are added to 100 µl of 1 mM DTNB, and the reaction is initiated by the addition of 50 µl of Boc-Ala-Ala-Met-S Benzyl (Bzl) to give a final concentration of 150 µM. The duration of the assay depends on color development, the rate of which is measured (O.D.$_{410}$) on a Dynatech MR 5000 microplate reader. Controls of sample and DTNB alone or DTNB and substrate alone are run.

For more sensitive comparisons of enzymatic activities, peptide thiobenzyl ester substrates are used to measure protease activities. The chymase substrate Suc-Phe-Leu-Phe-SBzl is purchased from BACHEM Bioscience Inc., Philadelphia, Pa. Z-Arg-SBzl (the tryptase substrate, Kam et al., *J. Biol. Chem.* 262, 3444–3451, 1987); Boc-Ala-Ala-AA-SBzl (AA=Asp, Met, Leu, Nle, or Ser), and Suc-Ala-Ala-Met-SBzl (Odake et al, *Biochemistry* 30, 2217–2227, 1991); Harper et al., *Biochemistry* 23, 2995–3002, 1984) are synthesized previously. Boc-Ala-Ala-Asp-SBzl is the substrate for Asp-ase and peptide thiobenzyl esters containing Met, Leu or Nle are substrates for Met-ase SP. Assays are performed at room temperature in 0.1 M, HEPES buffer, pH 7.5, containing 0.01 M CaCl$_2$ and 8% Me$_2$O using 0.34 mM 4,4'-dithiodipyridine (Aldrithiol-4, Aldrich Chemical Co., Milwaukee, Wis.) to detect HSBzl leaving group that reacts with 4,4'-dithiodipyridine to release thiopyridone ($\epsilon_{324}$=19800 M$^{-1}$ cm$^{-1}$, Grasetti and Murray, *Arch. Biochem. Biophys.* 119, 41–49, 1967). The initial rates are measured at 324 nm using a Beckman 35 spectrophotometer when 10–25 µl of an enzyme stock solution is added to a cuvette containing 2.0 ml of buffer, 150 µl of 4,4'-dithiodipyridine, and 25 µl of substrate. The same volume of substrate and 4,4'-dithiodipyridine are added to the reference cell in order to compensate for the background hydrolysis rate of the substrates. Initial rates are measured in duplicate for each substrate concentration and are averaged in each case. Substrate concentrations are 100–133 µM. It is shown that the polypeptide of SEQ ID NO: 2 and or SEQ ID NO: 6 have prostasin-like enzyme activity.

EXAMPLE 2

Identification of a Test Compound which Binds to a Prostasin-like Enzyme Polypeptide Purified prostasin-like enzyme polypeptides comprising a glutathione-S-transferase protein and absorbed onto glutathione-derivatized wells of 96-well microtiter plates are contacted with test compounds from a small molecule library at pH 7.0 in a physiological buffer solution. Prostasin-like enzyme polypeptides comprise the amino acid sequence shown in SEQ ID NO:2 or SEQ ID NO: 6. The test compounds comprise a fluorescent tag. The samples are incubated for 5 minutes to one hour. Control samples are incubated in the absence of a test compound.

The buffer solution containing the test compounds is washed from the wells. Binding of a test compound to a prostasin-like enzyme polypeptide is detected by fluorescence measurements of the contents of the wells. A test compound which increases the fluorescence in a well by at least 15% relative to fluorescence of a well in which a test compound was not incubated is identified as a compound which binds to a prostasin-like enzyme polypeptide.

EXAMPLE 3

Identification of a Test Compound which Decreases Prostasin-like Enzyme Activity Cellular extracts from the human colon cancer cell line HCT116 are contacted with test compounds from a small molecule library and assayed for prostasin-like enzyme activity. Control extracts, in the absence of a test compound, also are assayed. Protease activity can be measured using thiobenzylester substrates, as described in U.S. Pat. No. 5,500,344. For monitoring enzyme activities from granules and column fractions, assays are performed at room temperature using 0.5 mM 5,5'-dithiobis-(2-nitrobenzoic acid) (DTNB) (Sigma) to detect the HSBzl leaving group ($\epsilon_{410}$=13600 M$^{-1}$ cm$^{-1}$).

BLT-esterase activity is estimated using a microtiter assay (Green and Shaw, *Anal. Biochem.* 93, 223–226, 1979). Briefly, 50 µl of sample is added to 100 µl of 1 mM DTNB, made up in 10 mM HEPES, 1 mM CaCl$_2$, 1 mM MgCl$_2$, pH 7.2. The reaction is initiated by the addition of 50 µl of BLT (Sigma) to give a final concentration of 500 µM. For Metase determinations, 50 µl of dilutions of the sample in 0.1 M HEPES, 0.05 M CaCl$_2$, pH 7.5, are added to 100 µl of 1 mM DTNB, and the reaction is initiated by the addition of 50 µl of Boc-Ala-Ala-Met-S Benzyl (Bzl) to give a final concentration of 150 µM. The duration of the assay depends on color development, the rate of which is measured (O.D.$_{410}$) on a Dynatech MR 5000 microplate reader. Controls of sample and DTNB alone or DTNB and substrate alone are run.

For more sensitive comparisons of enzymatic activities, peptide thiobenzyl ester substrates are used to measure protease activities. The chymase substrate Suc-Phe-Leu-Phe-SBzl is purchased from BACHEM Bioscience Inc., Philadelphia, Pa. Z-Arg-SBzl (the tryptase substrate, Kam et al., *J. Biol. Chem.* 262, 3444–3451, 1987); Boc-Ala-Ala-AA-SBzl (AA=Asp, Met, Leu, Nle, or Ser), and Suc-Ala-Ala-Met-SBzl (Odake et al, *Biochemistry* 30, 2217–2227, 1991); Harper et al., *Biochemistry* 23, 2995–3002, 1984) are synthesized previously. Boc-Ala-Ala-Asp-SBzl is the substrate for Asp-ase and peptide thiobenzyl esters containing Met, Leu or Nle are substrates for Met-ase SP. Assays are performed at room temperature in 0.1 M, HEPES buffer, pH 7.5, containing 0.01 M $CaCl_2$ and 8% $Me_2O$ using 0.34 mM 4,4'-dithiodipyridine (Aldrithiol-4, Aldrich Chemical Co., Milwaukee, Wis.) to detect HSBzl leaving group that reacts with 4,4'-dithiodipyridine to release thiopyridone (324=19800 $M^{-1} cm^{-1}$, Grasefti and Murray, *Arch. Biochem. Biophys.* 119, 41–49, 1967). The initial rates are measured at 324 nm using a Beckman 35 spectrophotometer when 10–25 μl of an enzyme stock solution is added to a cuvette containing 2.0 ml of buffer, 150 μl of 4,4'-dithiodipyridine, and 25 μl of substrate. The same volume of substrate and 4,4'-dithiodipyridine are added to the reference cell in order to compensate for the background hydrolysis rate of the substrates. Initial rates are measured in duplicate for each substrate concentration and are averaged in each case. Substrate concentrations are 100–133 μM.

Alternatively, prostasin activity can be measured as described in Yu et al., *J. Biol. Chem.* 269, 11843–48, 1994.

A test compound which decreases prostasin-like enzyme activity of the extract relative to the control extract by at least 20% is identified as a prostasin-like enzyme inhibitor.

EXAMPLE 4

Identification of a Test Compound which Decreases Prostasin-like Enzyme Gene Expression A test compound is administered to a culture of the breast tumor cell line MDA-468 and incubated at 37° C. for 10 to 45 minutes. A culture of the same type of cells incubated for the same time without the test compound provides a negative control.

RNA is isolated from the two cultures as described in Chirgwin et al., *Biochem.* 18, 5294–99, 1979). Northern blots are prepared using 20 to 30 μg total RNA and hybridized with a $^{32}$P-labeled prostasin-like enzyme-specific probe at 65° C. in Express-hyb (CLONTECH). The probe comprises at least 11 contiguous nucleotides selected from the complement of SEQ ID NO:1 or SEQ ID NO: 5. A test compound which decreases the prostasin-like enzyme-specific signal relative to the signal obtained in the absence of the test compound is identified as an inhibitor of prostasin-like enzyme gene expression.

EXAMPLE 5

Treatment of a Breast Tumor with a Reagent which Specifically Binds to a Prostasin-like Enzyme Gene Product Synthesis of antisense prostasin-like enzyme oligonucleotides comprising at least 11 contiguous nucleotides selected from the complement of SEQ ID NO:1 or SEQ ID NO: 5 is performed on a Pharmacia Gene Assembler series synthesizer using the phosphoramidite procedure (Uhlmann et al., *Chem. Rev.* 90, 534–83, 1990). Following assembly and deprotection, oligonucleotides are ethanol-precipitated twice, dried, and suspended in phosphate-buffered saline (PBS) at the desired concentration. Purity of these oligonucleotides is tested by capillary gel electrophoreses and ion exchange HPLC. Endotoxin levels in the oligonucleotide preparation are determined using the Limulus Amebocyte Assay (Bang, *Biol. Bull.* (Woods Hole, Mass.) 105, 361–362, 1953).

An aqueous composition containing the antisense oligonucleotides at a concentration of 0.1–100 μM is injected directly into a breast tumor with a needle. The needle is placed in the tumors and withdrawn while expressing the aqueous composition within the tumor.

The breast tumor is monitored over a period of days or weeks. Additional injections of the antisense oligonucleotides can be given during that time. Metastasis of the breast tumor is suppressed due to decreased prostasin-like enzyme activity of the breast tumor cells.

EXAMPLE 6

Expression of Recombinant Human Prostasin-like Serine Protease

The *Pichia pastoris* expression vector pPICZB (Invitrogen, San Diego, Calif.) is used to produce large quantities of recombinant human prostasin-like serine protease polypeptides in yeast. The prostasin-like serine protease-encoding DNA sequence is derived from SEQ ID NO:1 or SEQ ID NO: 5. Before insertion into vector pPICZB, the DNA sequence is modified by well known methods in such a way that it contains at its 5'-end an initiation codon and at its 3'-end an enterokinase cleavage site, a His6 reporter tag and a termination codon. Moreover, at both termini recognition sequences for restriction endonucleases are added and after digestion of the multiple cloning site of pPICZ B with the corresponding restriction enzymes the modified DNA sequence is ligated into pPICZB. This expression vector is designed for inducible expression in *Pichia pastoris*, driven by a yeast promoter. The resulting pPICZ/md-His6 vector is used to transform the yeast.

The yeast is cultivated under usual conditions in 5 liter shake flasks and the recombinantly produced protein isolated from the culture by affinity chromatography (Ni-NTA-Resin) in the presence of 8 M urea. The bound polypeptide is eluted with buffer, pH 3.5, and neutralized. Separation of the polypeptide from the His6 reporter tag is accomplished by site-specific proteolysis using enterokinase (Invitrogen, San Diego, Calif.) according to manufacturer's instructions. Purified human prostasin-like serine protease polypeptide is obtained.

EXAMPLE 7

In Vivo Testing of Compounds/Target Validation

1. Acute Mechanistic Assays 1.1. Reduction in Mitogenic Plasma Hormone Levels

This non-tumor assay measures the ability of a compound to reduce either the endogenous level of a circulating hormone or the level of hormone produced in response to a biologic stimulus. Rodents are administered test compound (p.o., i.p., i.v., i.m., or s.c.). At a predetermined time after administration of test compound, blood plasma is collected. Plasma is assayed for levels of the hormone of interest. If the normal circulating levels of the hormone are too low and/or variable to provide consistent results, the level of the hormone may be elevated by a pre-treatment with a biologic stimulus (i.e., LHRH may be injected i.m. into mice at a dosage of 30 ng/mouse to induce a burst of testosterone synthesis). The timing of plasma collection would be adjusted to coincide with the peak of the induced hormone response. Compound effects are compared to a vehicle-treated control group. An F-test is preformed to determine if the variance is equal or unequal followed by a Student's t-test. Significance is p value$\leq$0.05 compared to the vehicle control group.

1.2. Hollow Fiber Mechanism of Action Assay

Hollow fibers are prepared with desired cell line(s) and implanted intraperitoneally and/or subcutaneously in rodents. Compounds are administered p.o., i.p., i.v., i.m., or s.c. Fibers are harvested in accordance with specific readout assay protocol, these may include assays for gene expression (bDNA, PCR, or Taqman), or a specific biochemical activity (i.e., cAMP levels. Results are analyzed by Student's t-test or Rank Sum test after the variance between groups is compared by an F-test, with significance at $p \leq 0.05$ as compared to the vehicle control group.

2. Subacute Functional In Vivo Assays 2.1. Reduction in Mass of Hormone Dependent Tissues This is another non-tumor assay that measures the ability of a compound to reduce the mass of a hormone dependent tissue (i.e., seminal vesicles in males and uteri in females). Rodents are administered test compound (p.o., i.p., i.v., i.m., or s.c.) according to a predetermined schedule and for a predetermined duration (i.e., 1 week). At termination of the study, animals are weighed, the target organ is excised, any fluid is expressed, and the weight of the organ is recorded. Blood plasma may also be collected. Plasma may be assayed for levels of a hormone of interest or for levels of test agent. Organ weights may be directly compared or they may be normalized for the body weight of the animal. Compound effects are compared to a vehicle-treated control group. An F-test is preformed to determine if the variance is equal or unequal followed by a Student's t-test. Significance is p value $\leq 0.05$ compared to the vehicle control group.

2.2. Hollow Fiber Proliferation Assay

Hollow fibers are prepared with desired cell line(s) and implanted intraperitoneally and/or subcutaneously in rodents. Compounds are administered p.o., i.p., i.v., i.m., or s.c. Fibers are harvested in accordance with specific readout assay protocol. Cell proliferation is determined by measuring a marker of cell number (i.e., MTT or LDH). The cell number and change in cell number from the starting inoculum are analyzed by Student's t-test or Rank Sum test after the variance between groups is compared by an F-test, with significance at $p \leq 0.05$ as compared to the vehicle control group.

2.3. Anti-angiogenesis Models 2.3.1. Corneal Angiogenesis

Hydron pellets with or without growth factors or cells are implanted into a micropocket surgically created in the rodent cornea. Compound administration may be systemic or local (compound mixed with growth factors in the hydron pellet). Corneas are harvested at 7 days post implantation immediately following intracardiac infusion of colloidal carbon and are fixed in 10% formalin. Readout is qualitative scoring and/or image analysis. Qualitative scores are compared by Rank Sum test. Image analysis data is evaluated by measuring the area of neovascularization (in pixels) and group averages are compared by Student's t-test (2 tail). Significance is $p<0.05$ as compared to the growth factor or cells only group.

2.3.2. Matrigel Angiogenesis

Matrigel, containing cells or growth factors, is injected subcutaneously. Compounds are administered p.o., i.p., i.v., i.m., or s.c. Matrigel plugs are harvested at predetermined time point(s) and prepared for readout. Readout is an ELISA-based assay for hemoglobin concentration and/or histological examination (i.e. vessel count, special staining for endothelial surface markers: CD31, factor-8). Readouts are analyzed by Student's t-test, after the variance between groups is compared by an F-test, with significance determined at $p<0.05$ as compared to the vehicle control group.

3. Primary Antitumor Efficacy 3.1. Early Therapy Models 3.1.1. Subcutaneous Tumor Tumor cells or fragments are implanted subcutaneously on Day 0. Vehicle and/or compounds are administered p.o., i.p., i.v., i.m., or s.c. according to a predetermined schedule starting at a time, usually on Day 1, prior to the ability to measure the tumor burden. Body weights and tumor measurements are recorded 2–3 times weekly. Mean net body and tumor weights are calculated for each data collection day. Anti-tumor efficacy may be initially determined by comparing the size of treated (T) and control (C) tumors on a given day by a Student's t-test, after the variance between groups is compared by an F-test, with significance determined at $p \leq 0.05$. The experiment may also be continued past the end of dosing in which case tumor measurements would continue to be recorded to monitor tumor growth delay. Tumor growth delays are expressed as the difference in the median time for the treated and control groups to attain a predetermined size divided by the median time for the control group to attain that size. Growth delays are compared by generating Kaplan-Meier curves from the times for individual tumors to attain the evaluation size. Significance is $p \leq 0.05$.

3.1.2. Intraperitoneal/Intracranial Tumor Models

Tumor cells are injected intraperitoneally or intracranially on Day 0. Compounds are administered p.o., i.p., i.v., i.m., or s.c. according to a predetermined schedule starting on Day 1. Observations of morbidity and/or mortality are recorded twice daily. Body weights are measured and recorded twice weekly. Morbidity/mortality data is expressed in terms of the median time of survival and the number of long-term survivors is indicated separately. Survival times are used to generate Kaplan-Meier curves. Significance is $p<0.05$ by a log-rank test compared to the control group in the experiment.

3.2. Established Disease Model

Tumor cells or fragments are implanted subcutaneously and grown to the desired size for treatment to begin. Once at the predetermined size range, mice are randomized into treatment groups. Compounds are administered p.o., i.p., i.v., i.m., or s.c. according to a predetermined schedule. Tumor and body weights are measured and recorded 2–3 times weekly. Mean tumor weights of all groups over days post inoculation are graphed for comparison. An F-test is preformed to determine if the variance is equal or unequal followed by a Student's t-test to compare tumor sizes in the treated and control groups at the end of treatment. Significance is $p \leq 0.05$ as compared to the control group. Tumor measurements may be recorded after dosing has stopped to monitor tumor growth delay. Tumor growth delays are expressed as the difference in the median time for the treated and control groups to attain a predetermined size divided by the median time for the control group to attain that size. Growth delays are compared by generating Kaplan-Meier curves from the times for individual tumors to attain the evaluation size. Significance is p value≦0.05 compared to the vehicle control group.

3.3. Orthotopic Disease Models 3.3.1. Mammary Fat Pad Assay

Tumor cells or fragments, of mammary adenocarcinoma origin, are implanted directly into a surgically exposed and reflected mammary fat pad in rodents. The fat pad is placed back in its original position and the surgical site is closed. Hormones may also be administered to the rodents to support the growth of the tumors. Compounds are administered p.o., i.p., i.v., i.m., or s.c. according to a predetermined schedule. Tumor and body weights are measured and recorded 2–3 times weekly. Mean tumor weights of all groups over days post inoculation are graphed for comparison. An F-test is preformed to determine if the variance is equal or unequal followed by a Student's t-test to compare tumor sizes in the treated and control groups at the end of treatment. Significance is p≦0.05 as compared to the control group.

Tumor measurements may be recorded after dosing has stopped to monitor tumor growth delay. Tumor growth delays are expressed as the difference in the median time for the treated and control groups to attain a predetermined size divided by the median time for the control group to attain that size. Growth delays are compared by generating Kaplan-Meier curves from the times for individual tumors to attain the evaluation size. Significance is p value≦0.05 compared to the vehicle control group. In addition, this model provides an opportunity to increase the rate of spontaneous metastasis of this type of tumor. Metastasis can be assessed at termination of the study by counting the number of visible foci per target organ, or measuring the target organ weight. The means of these endpoints are compared by Student's t-test after conducting an F-test, with significance determined at p≦0.05 compared to the control group in the experiment.

3.3.2. Intraprostatic Assay

Tumor cells or fragments, of prostatic adenocarcinoma origin, are implanted directly into a surgically exposed dorsal lobe of the prostate in rodents. The prostate is externalized through an abdominal incision so that the tumor can be implanted specifically in the dorsal lobe while verifying that the implant does not enter the seminal vesicles. The successfully inoculated prostate is replaced in the abdomen and the incisions throught e abdomen and skin are closed. Hormones may also be administered to the rodents to support the growth of the tumors. Compounds are administered p.o., i.p., i.v., i.m., or s.c. according to a predetermined schedule. Body weights are measured and recorded 2–3 times weekly. At a predetermined time, the experiment is terminated and the animal is dissected. The size of the primary tumor is measured in three dimensions using either a caliper or an ocular micrometer attached to a dissecting scope. An F-test is preformed to determine if the variance is equal or unequal followed by a Student's t-test to compare tumor sizes in the treated and control groups at the end of treatment. Significance is p≦0.05 as compared to the control group. This model provides an opportunity to increase the rate of spontaneous metastasis of this type of tumor. Metastasis can be assessed at termination of the study by counting the number of visible foci per target organ (i.e., the lungs), or measuring the target organ weight (i.e., the regional lymph nodes). The means of these endpoints are compared by Student's t-test after conducting an F-test, with significance determined at p≦0.05 compared to the control group in the experiment.

3.3.3. Intrabronchial Assay

Tumor cells of pulmonary origin may be implanted intrabronchially by malting an incision through the skin and exposing the trachea. The trachea is pierced with the beveled end of a 25 gauge needle and the tumor cells are inoculated into the main bronchus using a flat-ended 27 gauge needle with a 90° bend. Compounds are administered p.o., i.p., i.v., i.m., or s.c. according to a predetermined schedule. Body weights are measured and recorded 2–3 times weekly. At a predetermined time, the experiment is terminated and the animal is dissected. The size of the primary tumor is measured in three dimensions using either a caliper or an ocular micrometer attached to a dissecting scope. An F-test is preformed to determine if the variance is equal or unequal followed by a Student's t-test to compare tumor sizes in the treated and control groups at the end of treatment. Significance is p≦0.05 as compared to the control group. This model provides an opportunity to increase the rate of spontaneous metastasis of this type of tumor. Metastasis can be assessed at termination of the study by counting the number of visible foci per target organ (i.e., the contralateral lung), or measuring the target organ weight. The means of these endpoints are compared by Student's t-test after conducting an F-test, with significance determined at p≦0.05 compared to the control group in the experiment.

3.3.4. Intracecal Assay

Tumor cells of gastrointestinal origin may be implanted intracecally by making an abdominal incision through the skin and externalizing the intestine. Tumor cells are inoculated into the cecal wall without penetrating the lumen of the intestine using a 27 or 30 gauge needle. Compounds are administered p.o., i.p., i.v., i.m., or s.c. according to a predetermined schedule. Body weights are measured and recorded 2–3 times weekly. At a predetermined time, the experiment is terminated and the animal is dissected. The size of the primary tumor is measured in three dimensions using either a caliper or an ocular micrometer attached to a dissecting scope. An F-test is preformed to determine if the variance is equal or unequal followed by a Student's t-test to compare tumor sizes in the treated and control groups at the end of treatment. Significance is p≦0.05 as compared to the control group. This model provides an opportunity to increase the rate of spontaneous metastasis of this type of tumor. Metastasis can be assessed at termination of the study by counting the number of visible foci per target organ (i.e., the liver), or measuring the target organ weight. The means of these endpoints are compared by Student's t-test after conducting an F-test, with significance determined at p≦0.05 compared to the control group in the experiment.

4. Secondary (Metastatic) Antitumor Efficacy 4.1. Spontaneous Metastasis

Tumor cells are inoculated s.c. and the tumors allowed to grow to a predetermined range for spontaneous metastasis studies to the lung or liver. These primary tumors are then excised. Compounds are administered p.o., i.p., i.v., i.m., or s.c. according to a predetermined schedule which may include the period leading up to the excision of the primary tumor to evaluate therapies directed at inhibiting the early stages of tumor metastasis. Observations of morbidity and/or mortality are recorded daily. Body weights are measured and recorded twice weekly. Potential endpoints include survival time, numbers of visible foci per target organ, or target organ weight. When survival time is used as the endpoint the other values are not determined. Survival data is used to generate Kaplan-Meier curves. Significance is $p \leq 0.05$ by a log-rank test compared to the control group in the experiment. The mean number of visible tumor foci, as determined under a dissecting microscope, and the mean target organ weights are compared by Student's t-test after conducting an F-test, with significance determined at $p \leq 0.05$ compared to the control group in the experiment for both of these endpoints.

4.2. Forced Metastasis

Tumor cells are injected into the tail vein, portal vein, or the left ventricle of the heart in experimental (forced) lung, liver, and bone metastasis studies, respectively. Compounds are administered p.o., i.p., i.v., i.m., or s.c. according to a predetermined schedule. Observations of morbidity and/or mortality are recorded daily. Body weights are measured and recorded twice weekly. Potential endpoints include survival time, numbers of visible foci per target organ, or target organ weight. When survival time is used as the endpoint the other values are not determined. Survival data is used to generate Kaplan-Meier curves. Significance is $p<0.05$ by a log-rank test compared to the control group in the experiment. The mean number of visible tumor foci, as determined under a dissecting microscope, and the mean target organ weights are compared by Student's t-test after conducting an F-test, with significance at $p<0.05$ compared to the vehicle control group in the experiment for both endpoints.

EXAMPLE 8

Proliferation Inhibition Assay: Antisense Oligonucleotides Suppress the Growth of Cancer Cell Lines The cell line used for testing is the human colon cancer cell line HCT116. Cells are cultured in RPMI-1640 with 10–15% fetal calf serum at a concentration of 10,000 cells per milliliter in a volume of 0.5 ml and kept at 37° C. in a 95% air/5% $CO_2$ atmosphere.

Phosphorotbioate oligoribonucleotides are synthesized on an Applied Biosystems Model 380B DNA synthesizer using phosphoroamidite chemistry. A sequence of 24 bases complementary to the nucleotides at position 1 to 24 of SEQ ID NO:1 or SEQ ID NO: 5 is used as the test oligonucleotide. As a control, another (random) sequence is used: 5'-TCA ACT GAC TAG ATG TAC ATG GAC-3' (SEQ ID NO:7). Following assembly and deprotection, oligonucleotides are ethanol-precipitated twice, dried, and suspended in phosphate buffered saline at the desired concentration. Purity of the oligonucleotides is tested by capillary gel electrophoresis and ion exchange HPLC. The purified oligonucleotides are added to the culture medium at a concentration of 10 µM once per day for seven days.

The addition of the test oligonucleotide for seven days results in significantly reduced expression of human prostasin-like serine protease as determined by Western blotting. This effect is not observed with the control oligonucleotide. After 3 to 7 days, the number of cells in the cultures is counted using an automatic cell counter. The number of cells in cultures treated with the test oligonucleotide (expressed as 100%) is compared with the number of cells in cultures treated with the control oligonucleotide. The number of cells in cultures treated with the test oligonucleotide is not more than 30% of control, indicating that the inhibition of human prostasin-like serine protease has an anti-proliferative effect on cancer cells.

EXAMPLE 9

In vivo Testing of Compounds/Target Validation

1. Pain:

Acute Pain

Acute pain is measured on a hot plate mainly in rats. Two variants of hot plate testing are used: In the classical variant animals are put on a hot surface (52 to 56?C) and the latency time is measured until the animals show nocifensive behavior, such as stepping or foot licking. The other variant is an increasing temperature hot plate where the experimental animals are put on a surface of neutral temperature. Subsequently this surface is slowly but constantly heated until the animals begin to lick a hind paw. The temperature which is reached when hind paw licking begins is a measure for pain threshold.

Compounds are tested against a vehicle treated control group. Substance application is performed at different time points via different application routes (i.v., i.p., p.o., i.t., i.c.v., s.c., intradermal, transdermal) prior to pain testing.

Persistent Pain

Persistent pain is measured with the formalin or capsaicin test, mainly in rats. A solution of 1 to 5% formalin or 10 to 100 µg capsaicin is injected into one hind paw of the experimental animal. After formalin or capsaicin application the animals show nocifensive reactions like flinching, licking and biting of the affected paw. The number of nocifensive reactions within a time frame of up to 90 minutes is a measure for intensity of pain.

Compounds are tested against a vehicle treated control group. Substance application is performed at different time points via different application routes (i.v., i.p., p.o., i.t., i.c.v., s.c., intradermal, transdermal) prior to formalin or capsaicin administration.

Neuropathic Pain

Neuropathic pain is induced by different variants of unilateral sciatic nerve injury mainly in rats. The operation is performed under anesthesia. The first variant of sciatic nerve injury is produced by placing loosely constrictive ligatures around the common sciatic nerve. The second variant is the tight ligation of about the half of the diameter of the common sciatic nerve. In the next variant, a group of models is used in which tight ligations or transections are made of either the L5 and L6 spinal nerves, or the L % spinal nerve only. The fourth variant involves an axotomy of two of the three terminal branches of the sciatic nerve (tibial and common peroneal nerves) leaving the remaining sural nerve intact whereas the last variant comprises the axotomy of only the tibial branch leaving the sural and common nerves uninjured. Control animals are treated with a sham operation.

Postoperatively, the nerve injured animals develop a chronic mechanical allodynia, cold allodynioa, as well as a thermal hyperalgesia. Mechanical allodynia is measured by means of a pressure transducer (electronic von Frey Anesthesiometer, IITC Inc.-Life Science Instruments, Woodland Hills, SA, USA; Electronic von Frey System, Somedic Sales AB, Hörby, Sweden). Thermal hyperalgesia is measured by means of a radiant heat source (Plantar Test, Ugo Basile, Comerio, Italy), or by means of a cold plate of 5 to 10 ?C where the nocifensive reactions of the affected hind paw are counted as a measure of pain intensity. A further test for cold induced pain is the counting of nocifensive reactions, or duration of nocifensive responses after plantar administration of acetone to the affected hind limb. Chronic pain in general is assessed by registering the circadanian rhytms in activity (Surjo and Arndt, Universität zu Köln, Cologne, Germany), and by scoring differences in gait (foot print patterns; FOOTPRINTS program, Klapdor et al., 1997. A low cost method to analyse footprint patterns. J. Neurosci. Methods 75, 49–54).

Compounds are tested against sham operated and vehicle treated control groups. Substance application is performed at different time points via different application routes (i.v., i.p., p.o., i.t., i.c.v., s.c., intradermal, transdermal) prior to pain testing.

Inflammatory Pain

Inflammatory pain is induced mainly in rats by injection of 0.75 mg carrageenan or complete Freund's adjuvant into one hind paw. The animals develop an edema with mechanical allodynia as well as thermal hyperalgesia. Mechanical allodynia is measured by means of a pressure transducer (electronic von Frey Anesthesiometer, IITC Inc.-Life Science Instruments, Woodland Hills, SA, USA). Thermal hyperalgesia is measured by means of a radiant heat source (Plantar Test, Ugo Basile, Comerio, Italy, Paw thermal stimulator, G. Ozaki, University of California, USA). For edema measurement two methods are being used. In the first method, the animals are sacrificed and the affected hindpaws sectioned and weighed. The second method comprises differences in paw volume by measuring water displacement in a plethysmometer (Ugo Basile, Comerio, Italy).

Compounds are tested against uninflamed as well as vehicle treated control groups. Substance application is performed at different time points via different application routes (i.v., i.p., p.o., i.t., i.c.v., s.c., intradermal, transdermal) prior to pain testing.

Diabetic Neuropathic Pain

Rats treated with a single intraperitoneal injection of 50 to 80 mg/kg streptozotocin develop a profound hyperglycemia and mechanical allodynia within 1 to 3 weeks. Mechanical allodynia is measured by means of a pressure transducer (electronic von Frey Anesthesiometer, IITC Inc.-Life Science Instruments, Woodland Hills, SA, USA).

Compounds are tested against diabetic and non-diabetic vehicle treated control groups. Substance application is performed at different time points via different application routes (i.v., i.p., p.o., i.t., i.c.v., s.c., intradermal, transdermal) prior to pain testing.

2. Parkinson's Disease

6-Hydroxydopamine (6-OH-DA) Lesion

Degeneration of the dopaminergic nigrostriatal and striatopallidal pathways is the central pathological event in Parlinson's disease. This disorder has been mimicked experimentally in rats using single/sequential unilateral stereotaxic injections of 6-OH-DA into the medium forebrain bundle (MFB).

Male Wistar rats (Harlan Winkelmann, Germany), weighing 200±250 g at the beginning of the experiment, are used. The rats are maintained in a temperature- and humidity-controlled environment under a 12 h light/dark cycle with free access to food and water when not in experimental sessions. The following in vivo protocols are approved by the governmental authorities. All efforts are made to minimize animal suffering, to reduce the number of animals used, and to utilize alternatives to in vivo techniques.

Animals are administered pargyline on the day of surgery (Sigma, St. Louis, Mo., USA; 50 mg/kg i.p.) in order to inhibit metabolism of 6-OHDA by monoamine oxidase and desmethylirnipramine HCl (Sigma; 25 mg/kg i.p.) in order to prevent uptake of 6-OHDA by noradrenergic terminals. Thirty minutes later the rats are anesthetized with sodium pentobarbital (50 mg/kg) and placed in a stereotaxic frame. In order to lesion the DA nigrostriatal pathway 4 µl of 0.01% ascorbic acid-saline containing 8 µg of 6-OHDA HBr (Sigma) are injected into the left medial fore-brain bundle at a rate of 1 µl/min (2.4 mm anterior, 1.49 mm lateral, −2.7 mm ventral to Bregma and the skull surface). The needle is left in place an additional 5 min to allow diffusion to occur.

Stepping Test

Forelimb akinesia is assessed three weeks following lesion placement using a modified stepping test protocol. In brief, the animals are held by the experimenter with one hand fixing the hindlimbs and slightly raising the hind part above the surface. One paw is touching the table, and is then moved slowly sideways (5 s for 1 m), first in the forehand and then in the backhand direction. The number of adjusting steps is counted for both paws in the backhand and forehand direction of movement. The sequence of testing is right paw forehand and backhand adjusting stepping, followed by left paw forehand and backhand directions. The test is repeated three times on three consecutive days, after an initial training period of three days prior to the first testing. Forehand adjusted stepping reveals no consistent differences between lesioned and healthy control animals. Analysis is therefore restricted to backhand adjusted stepping.

Balance Test

Balance adjustments following postural challenge are also measured during the stepping test sessions. The rats are held in the same position as described in the stepping test and, instead of being moved sideways, tilted by the experimenter towards the side of the paw touching the table. This maneuver results in loss of balance and the ability of the rats to regain balance by forelimb movements is scored on a scale ranging from 0 to 3. Score 0 is given for a normal forelimb placement. When the forelimb movement is delayed but recovery of postural balance detected, score 1 is given. Score 2 represents a clear, yet insufficient, forelimb reaction, as evidenced by muscle contraction, but lack of success in recovering balance, and score 3 is given for no reaction of movement. The test is repeated three times a day on each side for three consecutive days after an initial training period of three days prior to the first testing.

Staircase Test (Paw Reaching)

A modified version of the staircase test is used for evaluation of paw reaching behavior three weeks following primary and secondary lesion placement. Plexiglass test boxes with a central platform and a removable staircase on each side are used. The apparatus is designed such that only the paw on the same side at each staircase can be used, thus providing a measure of independent forelimb use. For each test the animals are left in the test boxes for 15 min. The double staircase is filled with 7×3 chow pellets (Precision food pellets, formula: P, purified rodent diet, size 45 mg;

Sandown Scientific) on each side. After each test the number of pellets eaten (successfully retrieved pellets) and the number of pellets taken (touched but dropped) for each paw and the success rate (pellets eaten/pellets taken) are counted separately. After three days of food deprivation (12 g per animal per day) the animals are tested for 11 days. Full analysis is conducted only for the last five days.

MPTP Treatment

The neurotoxin 1-methyl-4-phenyl-1,2,3,6-tetrahydro-pyridine (MPTP) causes degeneration of mesencephalic dopaminergic (DAergic) neurons in rodents, non-human primates, and humans and, in so doing, reproduces many of the symptoms of Parkinson's disease. MPTP leads to a marked decrease in the levels of dopamine and its metabolites, and in the number of dopaminergic terminals in the striatum as well as severe loss of the tyrosine hydroxylase (TH)-immunoreactive cell bodies in the substantia nigra, pars compacta.

In order to obtain severe and long-lasting lesions, and to reduce mortality, animals receive single injections of MPTP, and are then tested for severity of lesion 7–10 days later. Successive MPTP injections are administered on days 1, 2 and 3. Animals receive application of 4 mg/kg MPTP hydrochloride (Sigma) in saline once daily. All injections are intraperitoneal (i.p.) and the MPTP stock solution is frozen between injections. Animals are decapitated on day 11.

Immunohistology

At the completion of behavioral experiments, all animals are anaesthetized with 3 ml thiopental (1 g/40 ml i.p., Tyrol Pharma). The mice are perfused transcardially with 0.01 M PBS (pH 7.4) for 2 min, followed by 4% paraformaldehyde (Merck) in PBS for 15 min. The brains are removed and placed in 4% paraformaldehyde for 24 h at 4° C. For dehydration they are then transferred to a 20% sucrose (Merck) solution in 0.1 M PBS at 4° C. until they sink. The brains are frozen in methylbutan at −20° C. for 2 min and stored at −70° C. Using a sledge microtome (mod. 3800-Frigocut, Leica), 25 μm sections are taken from the genu of the corpus callosum (AP 1.7 mm) to the hippocampus (AP 21.8 mm) and from AP 24.16 to AP 26.72. Forty-six sections are cut and stored in assorters in 0.25 M Tris buffer (pH 7.4) for immunohistochemistry.

A series of sections is processed for free-floating tyrosine hydroxylase (TH) immunohistochemistry. Following three rinses in 0.1 M PBS, endogenous peroxidase activity is quenched for 10 min in 0.3% $H_2O_2$±PBS. After rinsing in PBS, sections are preincubated in 10% normal bovine serum (Sigma) for 5 min as blocking agent and transferred to either primary anti-rat TH rabbit antiserum (dilution 1:2000).

Following overnight incubation at room temperature, sections for TH immunoreactivity are rinsed in PBS (2×10 min) and incubated in biotinylated anti-rabbit immunoglobulin G raised in goat (dilution 1:200) (Vector) for 90 min, rinsed repeatedly and transferred to Vectastain ABC (Vector) solution for 1 h. 3,3'-Diaminobenzidine tetrahydrochloride (DAB; Sigma) in 0.1 M PBS, supplemented with 0.005% $H_2O_2$, serves as chromogen in the subsequent visualization reaction. Sections are mounted on to gelatin-coated slides, left to dry overnight, counter-stained with hematoxylin dehydrated in ascending alcohol concentrations and cleared in butylacetate. Coverslips are mounted on entellan.

Rotarod Test

We use a modification of the procedure described by Rozas and. Labandeira-Garcia (1997), with a CR-1 Rotamex system (Columbus Instruments, Columbus, Ohio) comprising an IBM-compatible personal computer, a CIO-24 data acquisition card, a control unit, and a four-lane rotarod unit. The rotarod unit consists of a rotating spindle (diameter 7.3 cm) and individual compartments for each mouse. The system software allows preprogramming of session protocols with varying rotational speeds (0–80 rpm). Infrared beams are used to detect when a mouse has fallen onto the base grid beneath the rotarod. The system logs the fall as the end of the experiment for that mouse, and the total time on the rotarod, as well as the time of the fall and all the set-up parameters, are recorded. The system also allows a weak current to be passed through the base grid, to aid training.

3. Dementia

The Object Recognition Task

The object recognition task has been designed to assess the effects of experimental manipulations on the cognitive performance of rodents. A rat is placed in an open field, in which two identical objects are present. The rats inspects both objects during the first trial of the object recognition task. In a second trial, after a retention interval of for example 24 hours, one of the two objects used int the first trial, the 'familiar' object, and a novel object are placed in the open field. The inspection time at each of the objects is registered. The basic measures in the OR task is the time spent by a rat exploring the two object the second trial. Good retention is reflected by higher explortation times towards the novel than the 'familiar' object.

Administration of the putative cognition enhancer prior to the first trial predominantly allows assessment of the effects on acquisition, and eventually on consolidation processes. Administration of the testing compound after the first trial allows to assess the effects on consolidation processes, whereas administration before the second trial allows to measure effects on retrieval processes.

The passive avoidance task

The passive avoidance task assesses memory performance in rats and mice. The inhibitory avoidance apparatus consists of a two-compartment box with a light compartment and a dark compartment. The two compartments are separated by a guillotine door that can be operated by the experimenter. A threshold of 2 cm separates the two compartments when the guillotine door is raised. When the door is open, the illumination in the dark compartment is about 2 lux. The light intensity is about 500 lux at the center of the floor of the light compartment.

Two habituation sessions, one shock session, and a retention session are given, separated by inter-session intervals of 24 hours. In the habituation sessions and the retention session the rat is allowed to explore the apparatus for 300 sec. The rat is placed in the light compartment, facing the wall opposite to the guillotine door. After an accommodation period of 15 sec. the guillotine door is opened so that all parts of the apparatus can be visited freely. Rats normally avoid brighly lit areas and will enter the dark compartment within a few seconds.

In the shock session the guillotine door between the compartments is lowered as soon as the rat has entered the dark compartment with its four paws, and a scrambled 1 mA footshock is administered for 2 sec. The rat is removed from the apparatus and put back into its home cage. The procedure during the retention session is identical to that of the habituation sessions.

The step-through latency, that is the first latency of entering the dark compartment (in sec.) during the retention session is an index of the memory performance of the animal; the longer the latency to enter the dark compartment, the better the retention is. A testing compound in given half an hour before the shock session, together with 1 mg*kg$^{-1}$ scopolamine. Scopolamine impairs the memory performance during the retention session 24 hours later. If the test compound increases the enter latency compared with the scopolamine-treated controls, is is likely to possess cognition enhancing potential.

The Morris Water Escape Task

The Morris water escape task measures spatial orientation learning in rodents. It is a test system that has extensively been used to investigate the effects of putative therapeutic on the cognitive functions of rats and mice. The performance of an animal is assessed in a circular water tank with an escape platform that is submerged about 1 cm below the surface of the water. The escape platform is not visible for an animal swimming in the water tank. Abundant extra-maze cues are provided by the furniture in the room, including desks, computer equipment, a second water tank, the presence of the experimenter, and by a radio on a shelf that is playing softly.

The animals receive four trials during five daily acquisition sessions. A trial is started by placing an animal into the pool, facing the wall of the tank. Each of four starting positions in the quadrants north, east, south, and west is used once in a series of four trials; their order is randomized. The escape platform is always in the same position. A trial is terminated as soon as the animal had climbs onto the escape platform or when 90 seconds have elapsed, whichever event occurs first. The animal is allowed to stay on the platform for 30 seconds. Then it is taken from the platform and the next trial is started. If an animal did not find the platform within 90 seconds it is put on the platform by the experimenter and is allowed to stay there for 30 seconds. After the fourth trial of the fifth daily session, an additional trial is given as a probe trial: the platform is removed, and the time the animal spends in the four quadrants is measured for 30 or 60 seconds. In the probe trial, all animals start from the same start position, opposite to the quadrant where the escape platform had been positioned during acquisition.

Four different measures are taken to evaluate the performance of an animal during acquisition training: escape latency, traveled distance, distance to platform, and swimming speed. The following measures are evaluated for the probe trial: time (s) in quadrants and traveled distance (cm) in the four quadrants. The probe trial provides additional information about how well an animal learned the position of the escape platform. If an animal spends more time and swims a longer distance in the quadrant where the platform had been positioned during the acquisition sessions than in any other quadrant, one concludes that the platform position has been learned well.

In order to assess the effects of putative cognition enhancing compounds, rats or mice with specific brain lesions which impair cognitive functions, or animals treated with compounds such as scopolamine or MK-801, which interfere with normal learning, or aged animals which suffer from cognitive deficits, are used.

The T-maze Spontaneous Alternation Task

The T-maze spontaneous alternation task (TeMCAT) assesses the spatial memory performance in mice. The start arm and the two goal arms of the T-maze are provided with guillotine doors which can be operated manually by the experimenter. A mouse is put into the start arm at the beginning of training. The guillotine door is closed. In the first trial, the 'forced trial', either the left or right goal arm is blocked by lowering the guillotine door. After the mouse has been released from the start arm, it will negotiate the maze, eventually enter the open goal arm, and return to the start position, where it will be confined for 5 seconds, by lowering the guillotine door. Then, the animal can choose freely between the left and right goal arm (all guillotine-doors opened) diring 14 'free choice' trials. As soon a the mouse has entered one goal arm, the other one is closed. The mouse eventually returns to the start arm and is free to visit whichever goalarm it wants after having been confined to the start arm for 5 seconds. After completion of 14 free choice trials in one session, the animal is removed from the maze. During training, the animal is never handeled.

The per-cent alternations out of 14 trials is calculated. This percentage and the total time needed to complete the first forced trial and the subsequent 14 free choice trials (in s) is analyzed. Cognitive deficits are usually induced by an injection of scopolamine, 30 min before the start of the training session.

Scopolamine reduced the per-cent alternations to chance level, or below. A cognition enhancer, which is always administered before the training session, will at least partially, antagonize the scopolamine-induced reduction in the spontaneous alternation rate.

EXAMPLE 10

Tissue-specific Expression of Prostasin-Like Serine Protease

As a first step to establishing a role for prostasin-like serine protease in the pathogenesis of COPD, expression profiling of the gene was done using real-time quantitative PCR (TaqMan) with RNA samples isolated from a wide range of human cells and tissues. Total RNA samples were either purchased from commercial suppliers or purified in-house. Two panels of RNAs were used for profiling: a whole body organ panel (Table 1.) and a respiratory specific panel (Table 2).

Real-time quantitative PCR. This technique is a development of the kinetic analysis of PCR first described by Higuchi et al. (*BioTechnology* 10, 413–17, 1992; *BioTechnology* 11, 1026–30, 1993). The principle is that at any given cycle within the exponential phase of PCR, the amount of product is proportional to the initial number of template copies. PCR amplification is performed in the presence of an oligonucleotide probe (TaqMan probe) that is complementary to the target sequence and labeled with a fluorescent reporter dye and a quencher dye. During the extension phase of PCR, the probe is cleaved by the 5'-3' endonuclease activity of Taq DNA polymerase, releasing the fluorophore from the effect of the quenching dye (Holland et al., *Proc. Natl. Acad. Sci. U.S.A.* 88, 7276–80, 1991). Because the fluorescence emission increases in direct proportion to the amount of the specific amplified product, the exponential growth phase of PCR product can be detected and used to determine the initial template concentration (Heid et al., *Genome Res.* 6, 986–94, 1996, and Gibson et al., *Genome Res.* 6, 995–1001, 1996).

RNA extraction and cDNA preparation. Total RNA from each of the 'in-house' samples listed in Table 2 were isolated using Qiagen's (Crawley, West Sussex, UK) RNeasy system according to the manufacturer's protocol. The concentration of purified RNA was determined using RiboGreen RNA quantitation kit (Molecular Probes Europe, The Netherlands). RNA concentrations of the samples purchased from commercial-suppliers were also determined using RiboGreen. For the preparation of cDNA, 1 μg of total RNA was reverse transcribed using 200U of SUPERSCRIPT™ RNaseH⁻ Reverse Transcriptase (Life Technologies, Paisley, UK), 10 mM dithiothreitol, 0.5 mM of each dNTP, and 5 μM random hexamers (PE Applied Biosystems, Warrington, Cheshire, UK) in a final volume of 20 µl according to the manufacturer's protocol.

TaqMan quantitative analysis. Specific primers and probe were designed according to the recommendations of PE Applied Biosystems and are listed below:

Forward primer: 5'-AGAGTGGCGACCGCTACAAG-3' (SEQ ID NO:8)

Reverse primer: 5'-TGGTAGAGGCCGTCGCAG-3' (SEQ ID NO:9)

Probe: 5'-(FAM)-CGAGTCCAGCAGCGGCACCCT-TACT-3' (SEQ ID NO:10) where FAM=6-carboxy-fluorescein.

Quantification PCR was performed with 10 ng of reverse transcribed RNA from each sample. Each determination was done in duplicate.

The assay reaction mix was as follows: 1× final TaqMan Universal PCR Master Mix (from 2× stock) (PE Applied Biosystems, CA); 900 nM forward primer; 900 nM reverse primer; 200 nM probe; 10 ng cDNA; and water to 25 µl.

Each of the following steps were carried out once: pre PCR, 2 minutes at 50° C., and 10 minutes at 95° C.

The following steps are carried out 40 times: denaturation, 15 seconds at 95° C., annealing/extension, 1 minute at 60° C.

Real-time quantitative PCR was done using an ABI Prism 7700 Sequence Detector.

The $C_T$ value generated for each reaction was used to determine the initial template concentration (copy number) by interpolation from a universal standard curve. The level of expression of the target gene in each sample was calculated relative to the sample with the lowest expression of the gene.

The expression of prostasin-like enzyme in various human tissues is shown in FIG. 12. The highest levels of mRNA were detected in testis, bone marrow, spleen, and lung. Interestingly, expression of the enzyme was not detected in prostate or liver, which are tissues that exhibit high expression of prostasin itself (Yu et al., J. Biol. Chem. 270, 13483–13489). Moreover, prostasin is not expressed in testis, in contrast to the prostasin-like enzyme.

Expression of prostasin-like enzyme in lung was investigated further by analyzing the expression of the gene in some of the constituent cell types of the lung. This revealed consistent and abundant expression of prostasin-like enzyme in polymorphonuclear leukocytes (FIG. 13). Although there was relatively high expression of the gene in circulating monocytes from one donor, expression was not detected in monocytes from two other donors. Expression in trachea and alveolar type II cells was also clear.

The function of prostasin is unknown, although its widespread expression suggests its involvement in important biological processes. It is likely to be a membrane bound enzyme, indicated by the presence of a putative C-terminal membrane anchor, and, as such, may be involved in the processing of peptides and proteins at epithelial cell surfaces. The expression profile of prostasin-like enzyme is quite different to that of prostasin, perhaps indicating that these two proteases have different physiological functions. The relatively high expression of the enzyme in polymorphonuclear leukoctyes, one of the key inflammatory cell types of the lung, suggests that prostasin-like enzyme may be involved in inflammatory processes, and that dysregulation of the protease could play a significant role in the destruction of the lung matrix in diseases such as COPD. Prostasin-like enzyme, therefore, represents a potential therapeutic target for COPD.

TABLE 1

Human organ RNA panel used for real-time quantitative PCR. All samples were obtained from Clontech UK Ltd, Basingstoke, UK.

| Tissue | Cat. # |
|---|---|
| Adrenal gland | Human Panel V, K4004-1 |
| Bone marrow | Human Panel II, K4001-1 |
| Brain | Human Panel I, K4000-1 |
| Colon | Human Panel II, K4001-1 |
| Heart | Human Panel III, K4002-1 |
| Kidney | Human Panel I, K4000-1 |
| Liver | Human Panel I, K4000-1 |
| Lung | Human Panel I, K4000-1 |
| Mammary gland | Human Panel III, K4002-1 |
| Pancreas | Human Panel V, K4004-1 |
| Prostate | Human Panel III, K4002-1 |
| Salivary gland | Human Panel V, K4004-1 |
| Skeletal muscle | Human Panel III, K4002-1 |
| Small intestine | Human Panel II, K4001-1 |
| Spleen | Human Panel II, K4001-1 |
| Stomach | Human Panel II, K4001-1 |
| Testis | Human Panel III, K4002-1 |
| Thymus | Human Panel II, K4001-1 |
| Thyroid | Human Panel V, K4004-1 |
| Uterus | Human Panel III, K4002-1 |

TABLE 2

Human respiratory specific RNA panel used for real-time quantitative PCR.

| Tissue/cell type | Supplier, cat # |
|---|---|
| Lung (fetal) | Takara (Japan) |
| Lung | Clontech, Human Panel I, K4000-1 |
| Trachea | Clontech, Human Panel I, K4000-1 |
| Cultured human bronchial epithelial cells | In-house |
| Cultured airway smooth muscle cells | In-house |
| Cultured small airway epithelial cells | In-house |
| Primary cultured alveolar type II cells | In-house |
| Cultured H441 cells (Clara-like) | In-house |
| Freshly isolated polymorphonuclear leukocytes (neutrophils) | In-house |
| Freshly isolated monocytes | In-house |
| Cultured monocytes (macrophage-like) | In-house |

REFERENCES

1. Nicolson (1988) Organ specificity of tumor metastasis: Role of preferential adhesion, invasion and growth of malignant cells at specific secondary sites. *Cancer Met. Rev.* 7, 143–188.

2. Liotta et al. (1983) Tumor invasion and the extracellular matrix. *Lab. Invest.* 49, 639–649.

3. Vlodavsky et al. (1987) Endothelial cell-derived basic fibroblast growth factor: Synthesis and deposition into subendothelial extracellular matrix. *Proc. Natl. Acad. Sci. USA* 84, 2292–2296.

4. Folkman et al. (1980) A heparin-binding angiogenic protein—basic fibroblast growth factor—is stored within basement membrane. *Am. J. Pathol.* 130, 393400.

5. Cardon-Cardo et al. (1990) Expression of basic fibroblast growth factor in normal human tissues. *Lab. Invest.* 63, 832–840.

6. Vlodavsky et al. (1991) Extracellular sequestration and release of fibroblast growth factor: a regulatory mechanism? *Trends Biochem. Sci.* 16, 268–271.
7. Vlodavsky et al. (1993) Extracellular matrix-bound growth factors, enzymes and plasma proteins. In BASEMENT MEMBRANES: CELLULAR AND MOLECULAR ASPECTS Rohrbach & Timpl, eds., pp327–343. Academic Press Inc., Orlando, Fla.
8. Ross (1993) The pathogenesis of atherosclerosis: a perspective for the 1990s. *Nature (Lond.).* 362, 801–809.
9. McCarthy et al. (1986). Human fibronectin contains distinct adhesion- and motility-promoting domains for metastatic melanoma cells. *J. Cell Biol.* 102, 179–88.
10. Van Muijen et al. (1995) Properties of metastasizing and non-metastasizing human melanoma cells. *Recent Results in Cancer Research* 139, 104–22.
11. Price et al. (1997) The Biochemistry of Cancer Dissemination, in *Critical Reviews in Biochemistry and Mol. Biol.* 32, 175–253.

The invention claimed is:

1. An isolated and purified polynucleotide which encodes the amino acid sequence as shown in SEQ ID NO: 6.

2. The polynucleotide of claim 1 which comprises the nucleotide sequence as shown in SEQ ID NO: 5.

3. The polynucleotide of claim 1 which is a cDNA.

4. An expression construct, comprising; a coding sequence for the amino acid sequence as shown in SEQ ID NO: 6; and a promoter which is located upstream from the coding sequence and which controls expression of the coding sequence.

5. The expression construct of claim 4 wherein the coding sequence comprises a nucleotide sequence as shown in SEQ ID NO:5.

6. An isolated host cell comprising an expression construct, wherein the expression construct comprises: a coding sequence for a protein comprising the amino acid sequence as shown in SEQ ID NO: 6; and a promoter which is located upstream from the coding sequence and which controls expression of the coding sequence.

7. The host cell of claim 6 which is prokaryotic.

8. The host cell of claim 6 which is eukaryotic.

9. A method of producing a protein, comprising the steps of: culturing a host cell in a culture medium, wherein the host cell comprises an expression construct comprising (1) a coding sequence for a protein comprising an the amino acid sequence as shown in SEQ ID NO: 6 and (b) a promoter which is located upstream from the coding sequence and which controls expression of the coding sequence, wherein the step of culturing is carried out under conditions whereby the protein is expressed; and recovering the protein.

* * * * *

SEQUENCE LISTING

<160> NUMBER OF SEQ ID NOS: 6

<210> SEQ ID NO 1
<211> LENGTH: 786
<212> TYPE: DNA
<213> ORGANISM: Homo sapiens

<400> SEQUENCE: 1

```
atgagagggg tttcctgtct ccaggtcctg ctccttctgg tgctggcctg cgggcagccc      60
cgcatgtcca gtcggatcgt tgggggccgg gatggccggg acggagagtg gccgtggcag     120
gcgagcatcc agcatcgtgg ggcacacgtg tgcggggggt cgctcatcgc cccccagtgg     180
gtgctgacag cggcgcactg cttccccagg agggcactgc cagctgagta ccgcgtcgcc     240 ctggggcgc  tgcgtctggg ctccacctcg ccccgcacgc tctcggtgcc cgtgcgacgg     300
gtgctgctgc ccccggacta ctccgaggac ggggcccgcg gcgacctggc actgctgcag     360
ctgcgtcgcc cggtgcccct gagcgctcgc gtccaacccg tctgcctgcc cgtgcccggc     420
gcccgcccgc cgcccggcac accatgccgg gtcaccggct ggggcagcct ccgcccagga     480
gagtggcgac cgctacaagg agtaagggtg ccgctgctgg actcgcgcac ctgcgacggc     540
ctctaccacg tgggcgcgga cgtgcccag  gctgagcgca ttgtgctgcc tgggagtctg     600
tgtgccggct accccaggg  ccacaaggac gcctgccagg gtgattctgg gggacctctg     660
acctgcctgc agtctgggag ctgggtcctg gtgggcgtgg tgagctgggg caagggttgt     720
gccctgccca accgtccagg ggtctacacc agtgtggcca catatagccc ctggattcag     780
gctcgc                                                                786
```

<210> SEQ ID NO 2
<211> LENGTH: 262
<212> TYPE: PRT
<213> ORGANISM: Homo sapiens

<400> SEQUENCE: 2

```
Met Arg Gly Val Ser Cys Leu Gln Val Leu Leu Leu Val Leu Ala
  1               5                  10                  15

Cys Gly Gln Pro Arg Met Ser Ser Arg Ile Val Gly Gly Arg Asp Gly
                 20                  25                  30

Arg Asp Gly Glu Trp Pro Trp Gln Ala Ser Ile Gln His Arg Gly Ala
             35                  40                  45

His Val Cys Gly Gly Ser Leu Ile Ala Pro Gln Trp Val Leu Thr Ala
         50                  55                  60

Ala His Cys Phe Pro Arg Arg Ala Leu Pro Ala Glu Tyr Arg Val Arg
 65                  70                  75                  80

Leu Gly Ala Leu Arg Leu Gly Ser Thr Ser Pro Arg Thr Leu Ser Val
                 85                  90                  95
```

```
Pro Val Arg Arg Val Leu Leu Pro Pro Asp Tyr Ser Glu Asp Gly Ala
            100                 105                 110

Arg Gly Asp Leu Ala Leu Leu Gln Leu Arg Arg Pro Val Pro Leu Ser
        115                 120                 125

Ala Arg Val Gln Pro Val Cys Leu Pro Val Pro Gly Ala Arg Pro Pro
    130                 135                 140

Pro Gly Thr Pro Cys Arg Val Thr Gly Trp Gly Ser Leu Arg Pro Gly
145                 150                 155                 160

Glu Trp Arg Pro Leu Gln Gly Val Arg Val Pro Leu Leu Asp Ser Arg
                165                 170                 175

Thr Cys Asp Gly Leu Tyr His Val Gly Ala Asp Val Pro Gln Ala Glu
            180                 185                 190

Arg Ile Val Leu Pro Gly Ser Leu Cys Ala Gly Tyr Pro Gln Gly His
        195                 200                 205

Lys Asp Ala Cys Gln Gly Asp Ser Gly Gly Pro Leu Thr Cys Leu Gln
    210                 215                 220

Ser Gly Ser Trp Val Leu Val Gly Val Val Ser Trp Gly Lys Gly Cys
225                 230                 235                 240

Ala Leu Pro Asn Arg Pro Gly Val Tyr Thr Ser Val Ala Thr Tyr Ser
                245                 250                 255

Pro Trp Ile Gln Ala Arg
            260

<210> SEQ ID NO 3
<211> LENGTH: 343
<212> TYPE: PRT
<213> ORGANISM: Homo sapiens

<400> SEQUENCE: 3

Met Ala Gln Lys Gly Val Leu Gly Pro Gly Gln Leu Gly Ala Val Ala
1               5                   10                  15

Ile Leu Leu Tyr Leu Gly Leu Leu Arg Ser Gly Thr Gly Ala Glu Gly
            20                  25                  30

Ala Glu Ala Pro Cys Gly Val Ala Pro Gln Ala Arg Ile Thr Gly Gly
        35                  40                  45

Ser Ser Ala Val Ala Gly Gln Trp Pro Trp Gln Val Ser Ile Thr Tyr
    50                  55                  60

Glu Gly Val His Val Cys Gly Gly Ser Leu Val Ser Glu Gln Trp Val
65                  70                  75                  80

Leu Ser Ala Ala His Cys Phe Pro Ser Glu His His Lys Glu Ala Tyr
                85                  90                  95

Glu Val Lys Leu Gly Ala His Gln Leu Asp Ser Tyr Ser Glu Asp Ala
            100                 105                 110

Lys Val Ser Thr Leu Lys Asp Ile Ile Pro His Pro Ser Tyr Leu Gln
        115                 120                 125

Glu Gly Ser Gln Gly Asp Ile Ala Leu Leu Gln Leu Ser Arg Pro Ile
    130                 135                 140

Thr Phe Ser Arg Tyr Ile Arg Pro Ile Cys Leu Pro Ala Ala Asn Ala
145                 150                 155                 160

Ser Phe Pro Asn Gly Leu His Cys Thr Val Thr Gly Trp Gly His Val
                165                 170                 175

Ala Pro Ser Val Ser Leu Leu Thr Pro Lys Pro Leu Gln Gln Leu Glu
            180                 185                 190

Val Pro Leu Ile Ser Arg Glu Thr Cys Asn Cys Leu Tyr Asn Ile Asp
```

```
        195                200                205
Ala Lys Pro Glu Glu Pro His Phe Val Gln Glu Asp Met Val Cys Ala
    210                215                220

Gly Tyr Val Glu Gly Gly Lys Asp Ala Cys Gln Gly Asp Ser Gly Gly
225                230                235                240

Pro Leu Ser Cys Pro Val Glu Gly Leu Trp Tyr Leu Thr Gly Ile Val
                245                250                255

Ser Trp Gly Asp Ala Cys Gly Ala Arg Asn Arg Pro Gly Val Tyr Thr
            260                265                270

Leu Ala Ser Ser Tyr Ala Ser Trp Ile Gln Ser Lys Val Thr Glu Leu
        275                280                285

Gln Pro Arg Val Val Pro Gln Thr Gln Glu Ser Gln Pro Asp Ser Asn
    290                295                300

Leu Cys Gly Ser His Leu Ala Phe Ser Ser Ala Pro Ala Gln Gly Leu
305                310                315                320

Leu Arg Pro Ile Leu Phe Leu Pro Leu Gly Leu Ala Leu Gly Leu Leu
                325                330                335

Ser Pro Trp Leu Ser Glu His
            340

<210> SEQ ID NO 4
<211> LENGTH: 265
<212> TYPE: DNA
<213> ORGANISM: Homo sapiens
<220> FEATURE:
<221> NAME/KEY: misc_feature
<222> LOCATION: (1)...(265)
<223> OTHER INFORMATION: n = A,T,C or G

<400> SEQUENCE: 4
ccaggctgag cgcattgtgc tgcctgggag tctgtgtgcc ggctaccccc agggccacaa      60
ggacgcctgc caggtgtgca cccagcctnc ccagcctccg gagtcccctc cctgtgccca    120
gcaccctccc tccctgaact ccaggaccca ggacatccca actnaggctc aggatcctgg    180
cctccaacct agaggcacca cgncagggt ctggaaccct gagaactgaa gtcctgggag    240
ggctgggacc taggctcctc tttct                                           265

<210> SEQ ID NO 5
<211> LENGTH: 944
<212> TYPE: DNA
<213> ORGANISM: Homo sapiens

<400> SEQUENCE: 5
atgagagggg tttcctgtct ccaggtcctg ctccttctgg tgctggcctg cgggcagccc      60
cgcatgtcca gtcggatcgt tgggggccgg gatggccggg acggagagtg gccgtggcag    120
gcgagcatcc agcatcgtgg ggcacacgtg tgcgggggt cgctcatcgc ccccagtgg    180 gtgctgacag cggcgcactg cttccccagg agggcactgc agctgagta ccgcgtgcgc    240 ctggggcgc tgcgtctggg ctccaccctcg ccccgcacgc tctcggtgcc cgtgcgacgg    300
gtgctgctgc ccccggacta ctccgaggac ggggcccgcg gcgacctggc actgctgcag    360
ctgcgtcgcc cggtgcccct gagcgctcgc gtccaacccg tctgcctgcc cgtgcccggc    420
gcccgcccgc cgcccggcac accatgccgg gtcaccggct ggggcagcct ccgcccagga    480 gtgccccctcc cagagtggcg accgctacaa ggagtaaggg tgccgctgct ggactcgcgc    540
acctgcgacg gcctctacca cgtgggcgcg gacgtgcccc aggctgagcg cattgtgctg    600
```

```
cctgggagtc tgtgtgccgg ctaccccag ggccacaagg acgcctgcca gggtgattct      660 ggggacctc tgacctgcct gcagtctggg agctgggtcc tggtgggcgt ggtgagctgg      720
ggcaagggtt gtgccctgcc caaccgtcca ggggtctaca ccagtgtggc cacatatagc     780
ccctggattc aggctcgcgt caagattact aaatactaac cgggtgaagg agaacctgaa    840
gcaagtggtg ggggtcctca aaccacctgg ttcatacaag gacctgccta taaccaaaaa     900
ccttctgctt caagcaaaag ccaaaaagct aaggcaaccc aaca                      944
```

<210> SEQ ID NO 6
<211> LENGTH: 272
<212> TYPE: PRT
<213> ORGANISM: Homo sapiens

<400> SEQUENCE: 6

```
Met Arg Gly Val Ser Cys Leu Gln Val Leu Leu Leu Val Leu Ala
 1               5                  10                  15

Cys Gly Gln Pro Arg Met Ser Ser Arg Ile Val Gly Gly Arg Asp Gly
                20                  25                  30

Arg Asp Gly Glu Trp Pro Trp Gln Ala Ser Ile Gln His Arg Gly Ala
            35                  40                  45

His Val Cys Gly Gly Ser Leu Ile Ala Pro Gln Trp Val Leu Thr Ala
        50                  55                  60

Ala His Cys Phe Pro Arg Arg Ala Leu Pro Ala Glu Tyr Arg Val Arg
65                  70                  75                  80

Leu Gly Ala Leu Arg Leu Gly Ser Thr Ser Pro Arg Thr Leu Ser Val
                85                  90                  95

Pro Val Arg Arg Val Leu Leu Pro Pro Asp Tyr Ser Glu Asp Gly Ala
            100                 105                 110

Arg Gly Asp Leu Ala Leu Leu Gln Leu Arg Arg Pro Val Pro Leu Ser
        115                 120                 125

Ala Arg Val Gln Pro Val Cys Leu Pro Val Pro Gly Ala Arg Pro Pro
    130                 135                 140

Pro Gly Thr Pro Cys Arg Val Thr Gly Trp Gly Ser Leu Arg Pro Gly
145                 150                 155                 160

Val Pro Leu Pro Glu Trp Arg Pro Leu Gln Gly Val Arg Val Pro Leu
                165                 170                 175

Leu Asp Ser Arg Thr Cys Asp Gly Leu Tyr His Val Gly Ala Asp Val
            180                 185                 190

Pro Gln Ala Glu Arg Ile Val Leu Pro Gly Ser Leu Cys Ala Gly Tyr
        195                 200                 205

Pro Gln Gly His Lys Asp Ala Cys Gln Gly Asp Ser Gly Gly Pro Leu
    210                 215                 220

Thr Cys Leu Gln Ser Gly Ser Trp Val Leu Val Gly Val Val Ser Trp
225                 230                 235                 240

Gly Lys Gly Cys Ala Leu Pro Asn Arg Pro Gly Val Tyr Thr Ser Val
                245                 250                 255

Ala Thr Tyr Ser Pro Trp Ile Gln Ala Arg Val Lys Ile Thr Lys Tyr
            260                 265                 270
```